United States Patent [19]

Meier et al.

[11] Patent Number: 4,808,762
[45] Date of Patent: Feb. 28, 1989

[54] INSECTICIDAL CYCLOPROPYL-SUBSTITUTED DI(ARYL) COMPOUNDS

[75] Inventors: Gary A. Meier, Robbinsville; Scott M. Sieburth, Princeton; Thomas G. Cullen, Milltown, all of N.J.; John F. Engel, Washington Crossing, Pa.

[73] Assignee: FMC Corporation, Philadelphia, Pa.

[21] Appl. No.: 94,617

[22] Filed: Sep. 9, 1987

Related U.S. Application Data

[63] Continuation-in-part of Ser. No. 041,551, Sep. 23, 1987, abandoned.

[51] Int. Cl.⁴ ............... A01N 43/40; C07D 409/12
[52] U.S. Cl. .................................. 514/336; 514/337; 514/338; 514/345; 514/438; 514/443; 514/445; 514/452; 514/456; 514/464; 514/465; 514/469; 514/712; 546/269; 546/270; 546/274; 546/284; 546/290; 546/301; 546/302; 546/303; 514/717; 514/754; 514/764; 514/719; 549/49; 549/50; 549/58; 549/62; 549/66; 549/78; 549/80; 549/365; 549/398; 549/434; 549/445; 549/469; 568/49; 568/52; 568/56; 568/58; 568/635; 568/636; 568/637; 568/639; 568/643; 568/659; 568/661; 570/128; 570/129; 570/182; 570/185; 585/25

[58] Field of Search ............... 546/284, 270, 290, 301, 546/302, 303, 269, 774; 549/78, 80, 363, 62, 66, 49, 50, 58, 365, 398, 434, 445, 469; 568/49, 52, 56, 58, 635, 636, 637, 639, 643, 659, 661; 570/128, 129, 182, 185; 585/25; 514/336, 338, 345, 438, 452, 712, 717, 718, 721, 754, 764, 337, 443, 445, 456, 464, 465, 469, 719

[56] References Cited

U.S. PATENT DOCUMENTS 4,153,731 5/1979 Karrer .................... 568/637
4,575,517 3/1986 Knger et al. ............ 568/661
4,611,004 9/1986 Ackermann et al. ..... 568/636

FOREIGN PATENT DOCUMENTS 118534 7/1983 Japan ..................... 568/637
109505 6/1985 Japan ..................... 514/764
132901 7/1985 Japan ..................... 514/719

Primary Examiner—Bruce D. Gray
Attorney, Agent, or Firm—H. Robinson Ertelt; William Schmonsees

[57] ABSTRACT

Compounds of the formula

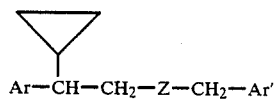

in which Ar is substituted or unsubstituted phenyl, naphthyl, or thienyl; Z is oxygen, sulfur, or methylene; and Ar' is 2-methyl[1,1'-biphenyl]-3-yl, 3-phenoxyphenyl, 4-fluoro-3-phenoxyphenyl, or 6-phenoxy-2-pyridyl exhibit pyrethroid-like insecticidal and acaricidal activity and are relatively harmless to aquatic fauna.

36 Claims, No Drawings

INSECTICIDAL CYCLOPROPYL-SUBSTITUTED DI(ARYL) COMPOUNDS

BACKGROUND OF THE INVENTION

This application is a continuation-in-part of application Ser. No. 041,551, filed Apr. 23, 1987 abandoned.

This invention relates to novel pyrethroid-like insecticides which effectively control infestations of undesirable insects and acarids and simultaneously display remarkably low toxicity to fish. Synthetic pyrethroids have been the focus of intensive research activity for more than a decade. The pioneering work of Elliott, as described in U.S. Pat. No. 4,024,163, established that synthetic pyrethroids could be synthesized with sufficient stability to light to be commercially attractive. The vast majority of these new pyrethroids are esters of substituted cyclopropanecarboxylic acids similar to those described by Elliott. Initially, compounds having the aforementioned structure were thought to be required for insecticidal activity; however, considerable effort has been successfully directed toward defining compounds which are nominally described as pyrethroids based upon similarities in molecular geometry and insecticidal activity. In some of these compounds only the ester linkage has been retained; in others the substituted cyclopropane ring has been retained; and in yet others neither the substituted cyclopropane ring nor the ester linkage has been retained. In the current invention an unsubstituted cyclopropane group is incorporated into pyrethroidlike compounds. These novel compounds lack the substituted cyclopropanecarboxylic acid moiety typical of the compounds described by Elliott and those who followed him. Further, these compounds display pyrethroid-like insecticidal activity while possessing remarkably low toxicity to fish in comparison with the notorious toxicity to fish exhibited by cyclopropanecarboxylates.

DESCRIPTION OF RELATED ART

U.S. Pat. No. 4,397,864 discloses a class of pyrethroid-like compounds hving the following subgeneric formula:

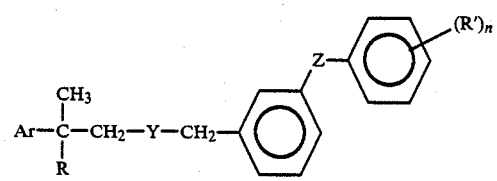

wherein
Ar is optionally substituted phenyl, optionally substituted naphthyl, or 1,3-benzodioxol-5-yl;
R is lower alkyl;
Y is O or S;
Z is O, S, or a carbonyl or methylene group;
R' is H, F, lower alkyl, or lower alkoxy; and
n is 1-5.

These compounds are alleged to have high insecticidal activity and low toxicity to fish.

U.S. Pat. No. 4,073,812 covers a closely related series of compounds having the generic formula:

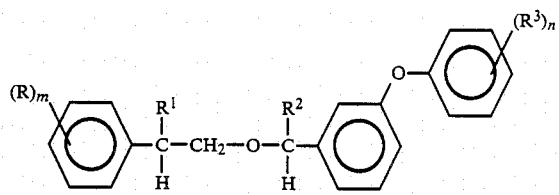

wherein
R is halogen, lower alkyl, or lower alkoxy;
m is 1 or 2;
$R^1$ is branched chain alkyl of 3-6 carbon atoms;
$R^2$ is hydrogen or alkynyl of 2-4 carbon atoms;
$R^3$ is fluorine; and
n is 0 or 1.

In all examples $R^1$ is isopropyl. All compounds are asserted to be insecticidal, some more than others, but there is no indication or assertion about the degree of toxicity to fish.

U.S. Pat. No. 4,562,213 covers another similar series of compounds of the formula:

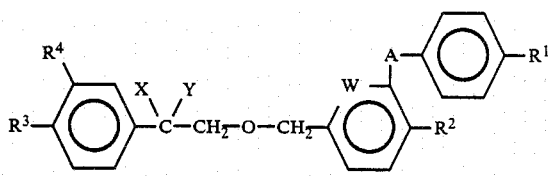

wherein
$R^1$ is hydrogen, halogen, or methyl;
$R^2$ is hydrogen or fluorine;
W is CH or N;
A is oxygen, methylene, or imino;
X and Y are both methyl or taken together form an optionally substituted cyclopropane ring;
$R^3$ and $R^4$ may be the same or different and are hydrogen, halogen, lower alkyl, lower alkoxy, lower fluoroalkoxy, or taken together form a methylenedioxy bridge. In all cases where A is oxygen, X and Y are taken together to form a cyclopropane ring or a substituted cyclopropane ring. These compounds are asserted to be insecticidal and acaricidal without any assertion relating to fish toxicity.

United Kingdom patent application GB No. 2 120 664A discloses a class of aromatic-substituted alkane derivatives having the following generic formula:

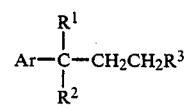

wherein
Ar stands for a substituted or unsubstituted phenyl or naphthyl group;
$R^1$ stands for a methyl, ethyl, or isopropyl group and
$R^2$ stands for a hydrogen atom or a methyl group or R[1] and R[2] taken together with the carbon to which they are attached represent a substituted or unsubstituted cycloalkyl group; and R[3] stands for the residue of an alcohol, R[3]OH, commonly found in natural or synthetic pyrethroids.

Examples of substituted or unsubstituted cycloalkyl groups named or exemplified by taking R[1] and R[2] together with the carbon to which they are attached are cyclopropyl, 2,2-dichlorocyclopropyl, cyclobutyl, cyclopentyl, and cyclohexyl. These compounds are asserted to be highly insecticidal and acaricidal and to have low toxicity to mammals and fish.

Belgian patent No. 902147 discloses a class of compounds having the following generic formula:

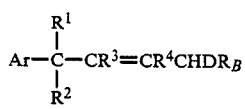

wherein
Ar represents a substituted or unsubstituted phenyl or naphthyl group;
R[1] and R[2] taken together with the carbon atom to which they are attached represent a substituted or unsubstituted cycloalkyl group of 3-6 carbon atoms;
R[3] and R[4], which may be the same or different, are hydrogen, halogen, or $C_1$-$C_6$ alkyl;
$R_B$ represents the residue of an alcohol, $R_B$CHDOH, which provides significant insecticidal activity when esterified with 1R,cis-3-(2,2-dibromoethenyl)-2,2-dimethylcyclopropanecarboxylic acid; and
D is hydrogen or cyano.

SUMMARY OF THE INVENTION

The compounds of this invention may be described as 2-(optionally substituted aryl)-2-cyclopropylethyl substituted-benzyl ethers and thioethers and 1-(optionally substituted aryl)-1-cyclopropyl-4-(substituted aryl)butanes. These compounds contain an asymmetric carbon atom; the invention thus includes individual stereoisomers as well as racemic and non-racemic mixtures of enantiomers of the instant compounds.

This invention also encompasses insecticidal compositions containing the pyrethroid ethers, thioethers, and butanes and their use for controlling insects. The compounds of this invention are effective for control of a wide variety of insects and acarids and may be expected to be useful in any situation for which pyrethroid insecticides are indicated. The compounds of this invention find particular utility in applications where there is a possibility of significant contamination of streams, rivers, and lakes by insecticidal material. Their low toxicity to fish will obviate concern about potential ecological problems associated with the use of pyrethroids in environments where such contamination is possible.

DETAILED DESCRIPTION

The 2-(optionally substituted aryl)-2-cyclopropylethyl substituted-benzyl ethers, thioethers, and the 1-(optionally substituted aryl)-1-cyclopropyl-4-(substituted aryl)butanes have the general formula:

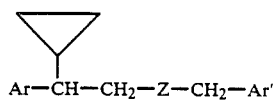

in which Ar is a substituted or unsubstituted phenyl, naphthyl, or thienyl. A substituted Ar may have one or two, not necessarily identical, substituents. Preferably Ar is phenyl and is monosubstituted at the 4-position. Preferred substituents include, but are not limited to, ($C_{1-6}$)alkyl, halo, ($C_{1-4}$)haloalkyl, ($C_{1-4}$)alkxoy, ($C_{1-4}$)haloalkoxy. Halo includes fluoro, chloro, and bromo. The term alkyl includes straight and branched chain alkyl groups having 1-6 carbon atoms, preferably 1-4 carbon atoms. The terms haloalkyl and haloalkoxy include alkyl and alkoxy groups in which one or more hydrogen atoms have been replaced by fluorine, chlorine, or bromine atoms including all combinations thereof. Further, the substituent may have the structure —A—(CR[1]R[2])n—A— where R[1] and R[2] are independently, hydrogen, halogen, or ($C_{1-2}$)alkyl, n is 1 or 2, and each A, which may be O, S, or $CH_2$, is bonded to a carbon atom of the aromatic ring, the carbons to which the A groups are attached being adjacent to each other in the ring. Illustrative of this mode of substitution are compounds in which Ar is 1,3-benzodioxolyl, 2,2-difluoro-1,3-benzodioxolyl, or 2,3-dihydro-2,2-dimethylbenzofuranyl. Typical Ar groups include:
phenyl, fluorophenyl, chlorophenyl, bromophenyl, preferably, 4-chlorophenyl;
methylphenyl, ethylphenyl, propylphenyl, isopropylphenyl, butylphenyl, isobutylphenyl, sec-butylphenyl, tert-butylphenyl, preferably methylphenyl;
methoxyphenyl, ethoxyphenyl, propoxyphenyl, isopropoxyphenyl, butoxyphenyl, isobutoxyphenyl, secbutoxyphenyl, or tert-butoxyphenyl, preferably methoxyphenyl or ethoxyphenyl;
fluoromethylphenyl, chloromethylphenyl, trifluoromethylphenyl, difluoromethylphenyl, fluoroethylphenyl, chloroethylphenyl, preferably trifluoromethylphenyl;
difluoromethoxyphenyl, trifluoromethoxyphenyl, 2-fluoroethoxyphenyl, 1,1,2,2-tetrafluoroethoxyphenyl, 2-bromo-1-1,2,2-tetrafluoroethoxyphenyl, preferably trifluoromethoxyphenyl or difluoromethoxyphenyl;
1,3-benzodioxol-5-yl, 2,2-difluoro-1,3-benzodioxol-5-yl, naphthyl, thienyl, 2,3-dihydro-2,2-dimethylbenzo-furan-5-yl, 2,2,3,3-tetrafluorobenzofuran-5-yl, and 2,3-dihydro-2,2-dimethylbenzofuran-7-yl;
Z is oxygen, sulfur, or methylene;
Ar' is 2-methyl[1,1'-biphenyl]-3-yl, 3-phenoxyphenyl, 4-fluoro-3-phenoxyphenyl, and 6-phenoxy-2-pyridyl, preferably 4-fluoro-3-phenoxyphenyl. Substitution of the phenyl, pyridyl, or phenoxy moieties with halogen or lower alkyl is within the scope of this invention.

The ether and thioether compounds of this invention are prepared by reacting an appropriate 2,2-disubstituted ethanol or thioethanol with sodium hydride, thus preparing the corresponding sodium ethoxide. The ethoxide or thioethoxide can, in turn, be reacted with an appropriately substituted benzyl halide to prepare the insecticidal ether or thioether. Example 1 describes the reaction of 2-cyclopropyl-2-(4-chlorophenyl)ethanol with sodium hydride in tetrahydrofuran and the reaction of the resulting sodium salt with (4-fluoro-3-phenoxyphenyl)methyl chloride to prepare (4-fluoro-3-phenoxyphenyl)methyl 2-cyclopropyl-2-(4-chlorophenyl)ethyl ether, Compound 16 of Table 1.

Numerous references describe the preparation of the substituted halides or preparation of the corresponding alcohols from which the halides may be prepared by conventional methods. The halides may be selected from chlorides, bromides, or iodides. Other leaving groups that may be readily displaced by a substituted ethoxide or thioethoxide may be substituted for the halogen atom of the benzyl halide. Examples of such leaving groups include, but are not limited to, methanesulfonate, trifluoromethanesulfonate, and p-toluenesulfonate.

The alcohol intermediates may be prepared from the aryl cyclopropyl ketones by conventional methods. In Example 1 the 4-chlorophenyl cyclopropyl ketone is reacted with sodium hydride and methyl triphenylphosphonium bromide to prepare 1-(4-chlorophenyl)-1-cyclopropylethene. Hydroboration of this olefin with bis(3-methyl-2-butyl)borane, followed by treatment with aqueous sodium hydroxide and hydrogen peroxide completes the synthesis of the ethanol from which the ether may be prepared as described above.

The substituted ethanol may be converted to the corresponding ethanethiol by reacting triphenylphosphine with diisopropyl azodicarboxylate and then reacting the resulting intermediate with the substituted ethanol. Quenching this reaction with thiolacetic acid produces the thiolacetate. Reduction of the thiolacetate produces the substituted thiol from which the thioether can be prepared by the same method described above for the ethers. Example 2 details the synthesis of (4-fluoro-3-phenoxy)methyl 2-cyclopropyl-2-(4-chlorophenyl)ethyl thioether, Compound 21 of Table 1 by this method.

Separation of the optical isomers can be effected by first preparing the 2,2-disubstituted acetic acid. One method for this preparation is to react the aryl cyclopropyl ketone with the anion prepared from 2-trimethylsilyl-1,3-dithiane and n-butyllithium. The resulting 2-[(aryl)cyclopropylmethylene]-1,3-dithiane may then be reacted with mercury (II) chloride, water, and methanol, producing methyl 2-aryl-2-cyclopropylacetate. Hydrolysis of the acetate to the acid and preparation of the acid chloride may be followed by reaction with (S)-4-(1-methylethyl)-2-oxazolidinone, previously prepared by reacting (S)-2-amino-3-methyl-1-butanol with phosgene. The two diastereomers of N-(2-aryl-2-cyclopropylacetyl)-4-(1-methylethyl)-2-oxazolidinone may then be separated chromatographically. Reduction of the individual diastereomers of the oxazolidinone with lithium aluminum hydride produces the (S) or (R)-2-aryl-2-cyclopropylethanols, each substantially free of the other antipode. In Example 3 details are provided for this method of preparing the two stereoisomers of (4-fluoro-3-phenoxyphenyl)methyl 2-cyclopropyl-2-(4-chlorophenyl)ethyl ether, Compounds 17 and 18 of Table 1.

The saturated, hydrocarbon compounds of this invention are prepared by reacting a substituted-phenyl cyclopropyl ketone with vinylmagnesium bromide to prepare the corresponding 1-(substituted phenyl)-1-cyclopropyl-2-propen-1-ol. Oxidation of this unsaturated alcohol yields 3-(substituted phenyl)-3-cyclopropylpropenal. The reaction of triphenylphosphine and a substituted-benzyl bromide yields the corresponding substituted benzyltriphenylphosphonium bromide which, in turn, can be reacted with the 3-(substituted phenyl)-3-cyclopropylpropenal in the presence of n-butyllithium to yield a 1-(substituted phenyl)-1-cyclopropyl-4-(substituted phenyl)butadiene. Hydrogenation of this butadiene produces the saturated insecticidal compounds of Formula I. Example 4 details the synthesis of 1-(4-chlorophenyl)-1-cyclopropyl-4-(3-phenoxyphenyl)butane, Compound 88 of Table 1, by this method.

Alternatively, the saturated, hydrocarbon compounds may be synthesized by reacting an appropriately substituted benzaldehyde with ethoxycarbonylmethylenetriphenylphosphorane, producing the corresponding ethyl 3-(substituted aryl)acrylate. Reduction of this ester with lithium aluminum hydride yields the corresponding 3-(substituted aryl)propanol. Reaction of this alcohol with phosphorous tribromide yields the propyl bromide which, in turn, is reacted with triphenylphosphine, producing the corresponding 3-(substituted aryl)propyltriphenylphosphonium bromide. The intermediate 1-(substituted phenyl)-1-cyclopropyl-4-(substituted aryl)-1-butene is prepared by reaction of the phosphonium bromide with the appropriate substituted-phenyl cyclopropyl ketone in the presence of n-butyllithium. Catalytic hydrogenation with Raney nickel completes the synthesis. By this method 1-(4-chlorophenyl)-1-cyclopropyl-4-(3-phenoxyphenyl)butane, Compound 88 of Table 1, was synthesized as described in Example 7.

Certain substituted-phenyl cyclopropyl ketones, e.g., 4-chlorophenyl cyclopropyl ketone, are commercially available. Others can be synthesized by starting with an appropriately substituted benzoic acid which can be converted to the acid chloride by the usual methods, e.g., by reaction with oxalyl chloride. Reaction of the acid chloride with N-methoxy-N-methylamine hydrochloride yields the corresponding substituted N-methoxy-N-methylbenzamide. The desired substituted-phenyl cyclopropyl ketone is then obtained by reacting the benzamide with cyclopropylmagnesium bromide. Example 5, Steps A-C, representative of this method, provide details for the synthesis of cyclopropyl (4trifluoromethylphenyl) ketone.

Alternatively, the substituted-phenyl cyclopropyl ketones may be prepared by reacting cyclopropanecarboxylic acid chloride with an appropriately substituted-phenyl compound in the presence of a Friedel-Crafts catalyst, e.g., aluminum chloride. In Example 6, Step A, cyclopropanecarboxylic acid chloride is reacted with ethoxybenzene in the presence of aluminum chloride, yielding cyclopropyl (4-ethoxyphenyl) ketone.

The intermediate butadienes of the formula:

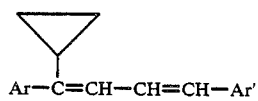

Ar—C=CH—CH=CH—Ar'

Ar and Ar' are defined as above are themselves insecticidal and acaricidal. Table 2 lists these compounds.

Also, the intermediate butenes of the formula:

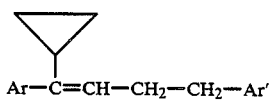

Ar—C=CH—CH$_2$—CH$_2$—Ar' wherein Ar and Ar' are defined as above are insecticidal and acaricidal. Table 3 lists these compounds. These olefins may exist in two configurations, the E and Z isomers. In the E isomer the cyclopropyl group and the —CH$_2$CH$_2$Ar' moiety are in a cis configuration in relation to the double bond and in the Z isomer these same moieties are situated in a trans configuration. In one instance an example of a Z isomer, Compound B13, was separated by rotating disk thin layer chromatography from a mixture of E and Z isomers. This enriched the residue, Compound B12, in the E isomer relative to the Z isomer. Comparisons of the insecticidal data for these compounds indicate that E isomers are significantly more active than the Z isomers.

The following examples provide additional details of the synthetic methods used to prepare the insecticidal ethers, thioethers, and hydrocarbons of this invention. Tables 1, 2, and 3 list these compounds. The compound numbers shown in each example are those assigned in these tables.

EXAMPLE 1

Synthesis of (4-fluoro-3-phenoxyphenyl)methyl 2-cyclopropyl-2-(4-chlorophenyl)ethyl ether [Compound 16]

Step A

Synthesis of 1-cyclopropyl-1-(4-chlorophenyl)ethene as an intermediate

Under a nitrogen atmosphere, a stirred suspension of 1.6 grams (0.063 mole) of 97% sodium hydride in 50 mL of dimethyl sulfoxide was heated at 80° C. for 90 minutes. The reaction mixture was cooled to ambient temperature, and 20.8 grams (0.056 mole) of methyl triphenylphosphonium bromide was added portionwise. Upon completion of addition, an additional 20 mL of dimethylsulfoxide was added to the reaction mixture which was then stirred at ambient temperature for 30 minutes and then at 60° C. for 30 minutes. The reaction mixture was cooled to ambient temperature, and 10.2 grams (0.056 mole) of cyclopropyl (4-chlorophenyl) ketone was added portionwise during a 15 minute period. Upon completion of addition, an additional 20 mL of dimethylsulfoxide was added, and the reaction mixture was stirred at ambient temperature for 18 hours. The reaction mixture was stirred with 100 mL of water which caused the precipitation of the by-product triphenylphosphine oxide. The aqueous layer and the precipitate were extracted with five 100 mL portions of hexane. The combined extracts were washed first with 80 mL of 1:1 dimethylsulfoxide:water and then with 80 mL of an aqueous, saturated sodium chloride solution. The organic layer was dried with magnesium sulfate and filtered. The filtrate was concentrated, yielding 10.9 grams of residual oil. A 1.2 gram sample from a previous run of this reaction was combined with the product of the reaction, and the 12.1 gram sample was distilled under reduced pressure, yielding 8.2 grams of 1-cyclopropyl-1-(4-chlorophenyl)ethene; b.p. 100°–105° C./34 mm. The nmr and ir spectra were consistent with the proposed structure.

Step B

Synthesis of 2-cyclopropyl-2-(4-chlorophenyl)ethanol as an intermediate

Under a nitrogen atmosphere, a stirred solution of 3.5 grams (0.019 mole) of 1-cyclopropyl-1-(4-chlorophenyl)ethene in 10 mL of distilled tetrahydrofuran was cooled to 0° C., and 29.5 mL (0.020 mole) of 0.68S M bis(3-methyl-2-butyl)borane in tetrahydrofuran was added via syringe during a 10 minute period. Upon completion of addition, the reaction mixture was stirred at 0° C. for 1.3 hours, at ambient temperature for 2.5 hours, and at 60° C. for 0.75 hour. The reaction mixture was cooled to 0° C., and 17 mL of methanol, 8.8 mL of aqueous 10% sodium hydroxide solution, and 8.0 mL of aqueous 30% hydrogen peroxide solution were sequentially added. Upon completion of addition, the reaction mixture was stirred at ambient temperature for 18 hours. The reaction mixture was heated at 60° C. for 30 minutes and then was cooled, after which 30 mL of an aqueous solution saturated with potassium carbonate was added. The aqueous layer was separated and extracted with three 30 mL portions of diethyl ether. The organic materials were combined and washed with 30 mL of an aqueous, saturated potassium carbonate solution. The organic layer was dried with magnesium sulfate/potassium carbonate and filtered. The filtrate was concentrated under reduced pressure, yielding 3.8 grams of 2-cyclopropyl-2-(4-chlorophenyl)ethanol. The nmr and ir spectra were consistent with the proposed structure.

Step C

Synthesis of (4-fluoro-3-phenoxyphenyl)methyl 2-cyclopropyl-2-(4-chlorophenyl)ethyl ether A stirred suspension of 0.1 gram (0.0044 mole) of sodium hydride in 5 mL of tetrahydrofuran was cooled to 0° C., and a solution of 0.8 gram (0.0041 mole) of 2-cyclopropyl-2-(4-chlorophenyl)ethanol in 2.5 mL of tetrahydrofuran was added via syringe during a two minute period. Upon completion of addition, the reaction mixture was allowed to warm to ambient temperature where it stirred for 30 minutes and then was heated to 55° C. where it stirred for 1.5 hours. The reaction mixture was cooled to ambient temperature, and a solution of 1.0 gram (0.0043 mole) of (4-fluoro-3-phenoxyphenyl)methyl chloride in 2.5 mL of tetrahydrofuran was added via syringe. Upon completion of addition, the reaction mixture stirred at ambient temperature for 20 hours and then was warmed to 60° C. where it stirred for 30 minutes. The reaction mixture was cooled, and 15 mL of water was added. The aqueous layer was removed and extracted with three 25 mL portions of hexanes. The organic materials were combined and dried with magnesium sulfate. The mixture was filtered, and the filtrate was concentrated under reduced pressure to a residual oil. The oil was purified by rotating disk thin layer chromatography using 5-10% ethyl acetate in hexanes for elution. The appropriate fractions were combined and concentrated under reduced pressure, yielding 0.65 gram of (4-fluoro3-phenoxyphenyl)-methyl 2-cyclopropyl-2-(4-chlorophenyl)ethyl ether. The nmr and the ir spectra were consistent with the proposed structure.

EXAMPLE 2

Synthesis of (4-fluoro-3-phenoxyphenyl)methyl 2-cyclopropyl-2-(4-chlorophenyl)ethyl thioether [Compound 21]

Step A

Synthesis of 2-cyclopropyl-2-(4-chlorophenyl)ethyl thiolacetate as an intermediate A stirred solution of 11.7 grams (0.045 mole) of triphenylphosphine in 75 mL of dry tetrahydrofuran was cooled to 0° C., and 9.0 grams (0.045 mole) of diisopropyl azodicarboxylate was added dropwise. Upon completion of addition, the reaction mixture was allowed to warm to ambient temperature where it stirred for 30 minutes. Successively, 4.4 grams (0.022 mole) of 2-cyclopropyl-2-(4-chlorophenyl)ethanol (prepared in Example 1, Step B) and 3.4 grams (0.045 mole) of thiolacetic acid were then added. The exothermic reaction caused the reaction mixture temperature to rise to 39° C. After cooling to ambient temperature the reaction mixture was stirred for 16 hours. The reaction mixture was then concentrated under reduced pressure to a residual oil. The oil was subjected to chromatography on silica gel using methylene chloride:heptane (1:4) as eluant. The appropriate fractions were combined and concentrated under reduced pressure, yielding 4.6 grams of 2-cyclopropyl-2-(4-chlorophenyl)ethyl thiolacetate as an oil. The nmr and the ir spectra were consistent with the proposed structure.

Step B

Synthesis of 2-cyclopropyl-2-(4-chlorophenyl)ethanethiol as an intermediate.

Under a nitrogen atmosphere a mixture of 1.2 grams (0.032 mole) of lithium aluminum hydride in dry tetrahydrofuran was stirred, and a solution of 4.1 grams (0.016 mole) of 2-cyclopropyl-2-(4-chlorophenyl)ethyl thiolacetate in 3 mL of tetrahydrofuran was added dropwise. Upon completion of addition, the reaction mixture was stirred at ambient temperature for 16 hours. Water was then carefully added dropwise to destroy excess lithium aluminum hydride. After the hydride was destroyed, 50 mL of additional water was added. The reaction mixture was extracted with several portions of diethyl ether. The combined extracts were dried with magnesium sulfate and filtered. The filtrate was concentrated under reduced pressure, yielding 3.4 grams of 2-cyclopropyl-2-(4-chlorphenyl)ethanethiol. The nmr and the ir spectra were consistent with the proposed structure.

Procedures analogous to Steps A and B are reported in Tetrahedron Letters, Vol. 22, No. 33, p 3119–3122, 1981.

Step C

Synthesis of (4-fluoro-3-phenoxyphenyl)methyl 2-cyclopropyl-2-(4-chlorophenyl)ethyl thioether This compound was prepared in a manner analogous to that of Example 1, Step C, using 1.0 gram (0.0046 mole) of 2-cyclopropyl-2-(4-chlorophenyl)ethanethiol, 0.97 gram (0.0041 mole) of (4-fluoro-3-phenoxyphenyl)-methyl chloride, and 0.22 gram (0.0055 mole) of sodium hydride in 12 mL of dry tetrahydrofuran. The yield of (4-fluoro-3-phenoxyphenyl)methyl 2-cyclopropyl-2-(4-chlorophenyl)ethyl thioether was 1.2 grams as an oil. The nmr and the ir spectra were consistent with the proposed structure.

EXAMPLE 3

Synthesis of the stereoisomers (A) and (B) of (4-fluoro-3-phenoxyphenyl)methyl 2-cyclopropyl-2-(4-chlorophenyl)ethyl ether [Compounds 17 and 18, respectively]

Step A

Synthesis of 2-[(4-chlorophenyl)cyclopropylmethylene]-1,3-dithiane as an intermediate A solution of 16.0 grams (0.083 mole) of 2-trimethylsilyl-1,3-dithiane in 80 mL of tetrahydrofuran was cooled to 0° C., and 39 mL (0.083 mole) of n-butyllithium (2.1M in hexane) was added. The reaction mixture was stirred for 15 minutes, and 15.0 grams (0.083 mole) of cyclopropyl (4-chlorophenyl) ketone in 40 mL of tetrahydrofuran was added via syringe during a five minute period. Upon completion of addition, the reaction mixture was stirred at 0° C. for 15 minutes and then was allowed to warm for 30 minutes. The reaction mixture was stirred with 100 mL of an aqueous solution saturated with sodium chloride, and then the two phases were separated. The aqueous phase was extracted with one portion of diethyl ether. The ether extract was combined with the organic phase, and this mixture was dried with magnesium sulfate and filtered through a pad of silica gel. The filtrate was concentrated under reduced pressure, yielding 24.0 grams of 2-[(4-chlorophenyl)cyclopropylmethylene]-1,3-dithiane as a solid, m.p. 91°–95° C. The nmr spectrum was consistent with the proposed structure.

Step B

Synthesis of methyl 2-cyclopropyl-2-(4-chlorophenyl)acetate as an intermediate A mixture of 10.0 grams (0.036 mole) of 2-[(4-chlorophenyl)cyclopropylmethylene]-1,3-dithiane, 24.0 grams (0.086 mole) of mercury (II) chloride, and 5 mL of water in 50 mL of methanol was stirred at ambient temperature for 18 hours. The reaction mixture was heated at reflux for one hour, cooled, and then was diluted with diethyl ether. The mixture was filtered through diatomaceous earth and then was dried with magnesium sulfate. The mixture was filtered through silica gel, and the filtrate was concentrated under reduced pressure, yielding 5.9 grams of methyl 2-cyclopropyl-2-(4-chlorophenyl)acetate as an oil. The nmr spectrum was consistent with the proposed structure. The reaction was run again to produce an additional 7.1 grams of the acetate.

Step C

Synthesis of 2-cyclopropyl-2-(4-chlorophenyl)acetic acid as an intermediate

A mixture of 13.0 grams (0.058 mole) of methyl 2-cyclopropyl-2-(4-chlorophenyl)acetate and 5.0 grams of an aqueous, 50% sodium hydroxide solution in 50 mL of methanol was stirred at ambient temperature for 18 hours. The reaction mixture was diluted with 150 mL of water, and the solution was decanted from a solid residue. The liquid portion was washed with three portions of diethyl ether. The combined ether washes were, in turn, washed with an aqueous, dilute sodium hydroxide solution. The combined aqueous layers were made acidic by the slow addition of aqueous, 10% hydrochloric acid. The acidified mixture was extracted with five portions of methylene chloride. The combined extracts were dried with sodium sulfate and filtered. The filtrate was concentrated under reduced pressure, yielding 7.4 grams of 2-cyclopropyl-2-(4-chlorophenyl)acetic acid as a solid, m.p. 95°–96° C.

Step D

Synthesis of (S)-4-(1-methylethyl)-2-oxazolidinone as an intermediate

A mixture of 9.4 grams (0.091 mole) of (S)-2-amino-3-methyl-1-butanol, 36 grams (0.0546 mole) of 85% potassium hydroxide, 175 mL of toluene, and 240 mL of water was stirred rapidly as 140 mL (0.273 mole) of a toluene solution containing 20% phosgene was added dropwise during a 15 minute period. Upon completion of addition, the resulting hot solution was stirred an additional 30 minutes. The reaction mixture was cooled, and the organic and aqueous layers were separated. The organic layer was washed with water and dried with magnesium sulfate. The mixture was filtered, and the filtrate was concentrated under reduced pressure, yielding 15.0 grams of (S)-4-(1-methylethyl)-2-oxazolidinone as a solid. Recrystallization from cyclohexane yielded purer compound, m.p. 71.5°–72.5° C.

Step E

Synthesis of (S)-N-[2-(4-chlorophenyl)-2-cyclopropylacetyl]-4-(1-methylethyl)-2-oxazolidinone and separation of its diastereomers (A) and (B) for use as intermediates A solution of 3.3 grams (0.016 mole) of 2-cyclopropyl-2-(4-chlorophenyl)acetic acid (prepared in Step C), 1.36 mL (0.016 mole) of oxalyl chloride, and two drops of N,N-dimethylformamide in 70 mL of diethyl ether was stirred at 0° C. for one hour. The reaction mixture was then allowed to warm to ambient temperature where it stirred for one hour.

In a separate reaction vessel a stirred solution of 2.0 grams (0.016 mole) of (S)-4-(1-methylethyl)-2-oxazolidinone in 50 mL of tetrahydrofuran was cooled to −78° C., and 6.25 mL (0.016 mole) of n-butyllithium (2.5 molar in hexane) was added dropwise. Upon completion of addition, the reaction mixture was stirred for 30 minutes, and then the 2-cyclopropyl-2-(4-chlorophenyl)acetyl chloride, prepared above, was added dropwise during several minutes. Upon completion of addition, the reaction mixture was stirred for an additional 30 minutes and then was poured into water. The organic layer was separated and washed with one portion of aqueous sodium bicarbonate. The organic layer was dried with magnesium sulfate and filtered. The filtrate was concentrated under reduced pressure to a residual oil. The oil was subjected to chromatography on silica gel using hexane:diethyl ether (3:1) as eluant. The appropriate fractions were combined and concentrated under reduced pressure, yielding 0.85 gram of diastereomer (A) and 0.8 gram of diastereomer (B) of (S)-N-[2-(4-chlorophenyl)-2-cyclopropylacetyl]-4-(1-methylethyl)-2-oxazolidinone. Upon standing, diastereomer (A) crystallized to a solid, m.p. 61°–64° C.

Step F

Synthesis of stereoisomer (A) of 2-cyclopropyl-2-(4-chlorophenyl)ethanol as an intermediate A stirred suspension of 0.31 gram (0.008 mole) of lithium aluminum hydride in 5 mL of tetrahydrofuran was cooled to 0° C., and 0.85 gram (0.0026 mole) of diastereomer (A) of (S)-N-[2-(4-chlorophenyl)-2-cyclopropylacetyl]-4-(1-methylethyl)-2-oxazolidinone was added. Upon completion of addition, the reaction mixture was stirred for 45 minutes, and then 15 mL of hexane was added to the reaction mixture. This was followed by the careful addition of 0.3 mL of water, 0.3 mL of aqueous 15% sodium hydroxide, and 0.9 mL of water. The reaction mixture was stirred with magnesium sulfate and filtered through a pad of silica gel. The filtrate was concentrated under reduced pressure to a residual oil. The oil was subjected to chromatography on silica gel using diethyl ether:hexane (1:1) as eluant. The appropriate fractions were combined and concentrated under reduced pressure, yielding 0.4 gram of stereoisomer (A) of 2-cyclopropyl-2-(4-chlorophenyl)ethanol as an oil.

Step G

Synthesis of stereoisomer (A) of (4-fluoro-3-phenoxyphenyl)methyl 2-cyclopropyl-2-(4-chlorophenyl)ethyl ether Under a nitrogen atmosphere a suspension of 0.06 gram (0.0024 mole) of 97% sodium hydride in 2.2 mL of dimethylformamide was stirred, and a solution of 0.40 gram (0.002 mole) of stereoisomer (A) of 2-cyclopropyl-2-(4-chlorophenyl)ethyl ethanol in 1.0 mL of dimethylformamide was slowly added. Upon completion of addition, the reaction mixture was stirred for 1.5 hours, and then a solution of 0.46 gram (0.0019 mole) of (4-fluoro-3-phenoxyphenyl)methyl chloride in 1.0 mL of dimethylformamide was added. Upon completion of addition, the reaction mixture was stirred for one hour, and then 2-3 mL of water was added. The mixture was poured into 75 mL of aqueous, 10% hydrochloric acid and then was extracted with two 50 mL portions of hexane. The combined hexane layers were washed with 25 mL of a saturated, aqueous solution of sodium chloride. The organic layer was dried with sodium sulfate and filtered. The filtrate was concentrated under reduced pressure to a residual oil. The oil was subjected to rotating disk thin layer chromatography on silica gel using diethyl ether: hexane (19:1) as eluant. The appropriate fractions were combined and concentrated under reduced pressure, yielding 0.55 gram of stereoisomer (A) of (4-fluoro-3-phenoxyphenyl)methyl 2-cyclopropyl-2-(4-chlorophenyl)ethyl ether as an oil. The nmr spectrum was consistent with the proposed structure. $[\alpha]_D^{25} = (+)22.19°$.

Step H

Synthesis of stereoisomer (B) of 2-cyclopropyl-2-(4-chlorophenyl)ethanol as an intermediate.

This compound was prepared in a manner analogous to that of Step F, using 0.80 gram (0.0025 mole) of diastereomer (B) of (S)-N-[2-(4-chlorophenyl)-2-cyclopropylacetyl]-4-(1-methylethyl)-2-oxazolidinone (prepared in Example 3, Step E) and 0.30 gram (0.008 mole) of lithium aluminum hydride in 15 mL of tetrahydrofuran. The yield of stereoisomer (B) of 2-cyclopropyl-2-(4-chlorophenyl)ethanol was 0.45 gram as an oil.

Step I

Synthesis of stereoisomer (B) of (4-fluoro-3-phenoxyphenyl)methyl 2-cyclopropyl-2-(4-chlorophenyl) -

This compound was prepared in a manner analogous to that of Step G, using 0.40 gram (0.0020 mole) of stereoisomer (B) of 2-cyclopropyl-2-(4-chlorophenyl)ethanol (prepared in Step H), 0.46 gram (0.0019 mole) of (4-fluoro-3-phenoxyphenyl)methyl chloride, and 0.06 gram (0.0024 mole) of sodium hydride in 4.2 mL of dimethylformamide. The yield of stereoisomer (B) of (4-fluoro-3-phenoxyphenyl)methyl 2-cyclopropyl-2-(4-chlorophenyl)ethyl ether was 0.56 gram as an oil. The nmr spectrum was consistent with the proposed structure. $[\alpha]_D^{25} = (-)20.64°$

EXAMPLE 4

Synthesis of 1-(4-chlorophenyl)-1-cyclopropyl-4-(3-phenoxyphenyl)butane [Compound 88]

Step A

Synthesis of 1-(4-chlorophenyl)-1-cyclopropyl-2-propen-1-ol as an intermediate

A 1.0 M solution of vinylmagnesium bromide in tetrahydrofuran (110 mL, 0.11 mole) was stirred, and a solution of 18.1 grams (0.1 mole) of commercially available 4-chlorophenyl cyclopropyl ketone in 50 mL of dry tetrahydrofuran was added dropwise during a one hour period. The exothermic reaction caused the reaction mixture to warm to 45° C. Upon completion of addition, the reaction mixture was stirred for two hours as it cooled to ambient temperature. The reaction was quenched with the addition of 50 mL of a saturated, aqueous solution of ammonium chloride. The mixture was extracted with two 50 mL portions of diethyl ether. The combined extracts were dried with potassium carbonate and filtered. The filtrate was concentrated under reduced pressure, yielding 20.0 grams of 1-(4-chlorophenyl)-1-cyclopropyl-2-propen-1-ol.

Step B

Synthesis of 3-(4-chlorophenyl)-3-cyclopropylpropenal as an intermediate

To a stirred solution of 40.3 grams (0.192 mole) of pyridinium chlorochromate in 210 mL of methylene chloride was added a solution of 20.0 grams (0.096 mole) of 1-(4-chlorophenyl)-1-cyclopropyl-2-propen-1-ol in 25 mL of methylene chloride in one portion. Upon completion of addition, the reaction mixture was stirred for two hours. A supernatent layer was decanted from a residue, and the residue was extracted with diethyl ether. The supernatent layer was combined with the ether extracts, and the combination was washed with two 100 mL portions of an aqueous 5% sodium hydroxide solution, 100 mL of an aqueous 5% hydrochloric acid solution, and then with 50 mL of an aqueous solution saturated with sodium bicarbonate. The organic layer was dried with sodium sulfate and filtered. The filtrate was concentrated under reduced pressure to a residue. The residue was subjected to column chromatography on silica gel. Elution was accomplished using 5% diethyl ether in hexane. The appropriate fractions were combined and concentrated under reduced pressure, yielding 6.8 grams of 3-(4-chlorophenyl)-3-cyclopropylpropenal.

Step C

Synthesis of 3-phenoxyphenylmethyltriphenylphosphonium chloride as an intermediate A stirred solution of 5.0 grams (0.0228 mole) of 3-phenoxyphenylmethyl chloride and 5.6 grams (0.0217 mole) of triphenyl phosphine in 50 mL of dry toluene was heated at reflux for 8 hours. The reaction mixture was cooled and filtered to collect a solid. The solid was washed with pentane and dried, yielding 4.6 grams of 3-phenoxyphenylmethyltriphenylphosphonium chloride. The nmr spectrum was consistent with the proposed structure.

Step D

Synthesis of 1-(4-chlorophenyl)-1-cyclopropyl-4-(3-phenoxyphenyl)-1,3-butadiene (Compound A5) as an intermediate A stirred solution of 4.4 mL (0.011 mole) of n-butyllithium (2.5 molar in hexane) in 100 mL of dry tetrahydrofuran was cooled to −78° C., and 4.6 grams (0.01 mole) of 3-phenoxyphenylmethyltriphenylphosphonium chloride was quickly added. Upon completion of addition, the reaction mixture was stirred at −78° C. for one hour and then was allowed to warm to −20° C. where it stirred for one hour. The reaction mixture was cooled to −78° C., and 2.1 grams (0.01 mole) of 3-(4-chlorophenyl)-3-cyclopropylpropenal (prepared in Step B) in 10 mL of tetrahydrofuran was added during a 15 minute period. Upon completion of addition, the reaction mixture was allowed to warm to ambient temperature where it stirred for two hours. The reaction was quenched with the addition of 15 mL of aqueous 10% hydrochloric acid solution. The mixture was extracted with diethyl ether. The combined extracts were dried with sodium sulfate and filtered. The filtrate was concentrated under reduced pressure to a residue. The residue was subjected to column chromatography on silica gel. Elution was accomplished using 5% diethyl ether in hexane. The appropriate fractions were combined and concentrated under reduced pressure, yielding 3.2 grams of 1-(4-chlorophenyl)-1-cyclopropyl-4-(3-phenoxyphenyl)1,3-butadiene.

Step E

Synthesis of 1-(4-chlorophenyl)-1-cyclopropyl-4-(3-phenoxyphenyl)butane (Compound 88)

A mixture of 2.3 grams (0.006 mole) of 1-(4-chlorophenyl)-1-cyclopropyl-4-(3-phenoxyphenyl)-1,3-butadiene, 2.3 grams (0.002 mole) of 10% palladium on carbon, 0.25 gram (0.0002 mole) of tris(triphenylphosphine)rhodium (I) chloride, and 25 mL of benzene in 100 mL of ethanol was hydrogenated at 40° C. using a Parr hydrogenator. Upon completion of the uptake of the theoretical amount of hydrogen (two hours), the reaction mixture was cooled and filtered. The filtrate was concentrated under reduced pressure to a residue. The residue was taken up in hexane and filtered. The filtrate was dried with sodium sulfate and filtered again. The filtrate was concentrated under reduced pressure to a residue. The residue was subjected to rotating disk thin layer chromatography. Elution was accomplished using 20% toluene in hexane. The appropriate fractions were combined and concentrated under reduced pressure, yielding 0.52 gram of 1-(4-chlorophenyl)-1-cyclopropyl4-(3-phenoxyphenyl)butane as an oil. The nmr spectrum was consistent with the proposed structure.

EXAMPLE 5

Synthesis of 1-cyclopropyl-1-(4-trifluoromethylphenyl)-4-(4-fluoro-3-phenoxyphenyl)butane [Compound 99]

Step A

Synthesis of 4-trifluoromethylbenzoyl chloride as an intermediate

A stirred solution of 20.0 grams (0.105 mole) of 4-trifluoromethylbenzoic acid and four drops of dimethylformamide in 300 mL of methylene chloride was cooled to 0°-10° C., and 14.7 grams (0.116 mole) of oxalyl chloride was added. Upon completion of addition, the reaction mixture was allowed to warm to ambient temperature where it stirred for 18 hours. The reaction mixture was then concentrated under reduced pressure, yielding 21.9 grams of 4-trifluoromethylbenzoyl chloride as a semi-solid. The reaction was repeated.

Step B

Synthesis of N-methoxy-N-methyl-4-trifluoromethylbenzamide as an intermediate

To a stirred suspension of 19.9 grams (0.204 mole) of N-methoxy-N-methylamine hydrochloride in 500 mL of methylene chloride was added 39.3 grams (0.388 mole) of triethylamine. Upon completion of addition, the reaction mixture was stirred for ten minutes, and a solution of 38.4 grams (0.185 mole) of 4-trifluoromethylbenzoyl chloride in 25 mL of methylene chloride was added dropwise. Upon completion of addition, the reaction mixture was stirred at ambient temperature for 18 hours. The reaction mixture was then stirred vigorously with 300 mL of water. The aqueous layer was separated from the organic layer and washed with three portions of methylene chloride. The washes were combined with the organic layer, and the combination was dried with magnesium sulfate. The mixture was filtered, and the filtrate was concentrated under reduced pressure, yielding 42.5 grams of N-methoxy-N-methyl-4-trifluoromethylbenzamide as an oil. The nmr spectrum was consistent with the proposed structure.

Step C

Synthesis of cyclopropyl (4-trifluoromethylphenyl) ketone as an intermediate

Under a nitrogen atmosphere a vigorously stirred solution of 42.5 grams (0.182 mole) of N-methoxy-N-methyl-4-trifluoromethylbenzamide in 250 mL of dry tetrahydrofuran was cooled to 0°-10° C., and 41.7 grams (0.0287 mole) of freshly prepared cyclopropylmagnesium bromide in 170 mL of tetrahydrofuran was added rapidly dropwise. Upon completion of addition, the reaction mixture was allowed to warm to ambient temperature where it stirred for 60 hours. The reaction mixture was then concentrated under reduced pressure to a residue. The residue was taken up in water and extracted with four portions of methylene chloride. The combined extracts were dried with magnesium sulfate and filtered. The filtrate was passed through a pad of silica gel and was concentrated under reduced pressure yielding, 34.6 grams of cyclopropyl (4-trifluoromethylphenyl) ketone. The nmr spectrum was consistent with the proposed structure.

Step D

Synthesis of 1-cyclopropyl-1-(4-trifluoromethylphenyl)-2-propen-1-ol as an intermediate This compound was prepared in a manner analogous to that f Example 4, Step A, using 10.0 grams (0.05 mole) of cyclopropyl (4-trifluoromethylphenyl) ketone and 50 mL (0.05 mole) of vinylmagnesium bromide (1.0M in tetrahydrofuran) and 25 mL of tetrahydrofuran. The yield of 1-cyclopropyl-1-(4-trifluoromethylphenyl)-2-propen-1-ol was 11.6 grams. The nmr spectrum was consistent with the proposed structure.

Step E

Synthesis of 3-cyclopropyl-3-(4-trifluoromethylphenyl)propenal as an intermediate This compound was prepared in a manner analogous to that of Example 4, Step B, using 11.1 grams (0.046 mole) of 1-cyclopropyl-1-(4-trifluoromethylphenyl)-2-propen-1-ol and 19.7 grams (0.091 mole) of pyridinium chlorochromate in 100 mL of methylene chloride. The yield of 3-cyclopropyl-3-(4-trifluoromethylphenyl)propenal was 5.5 grams

Step F

Synthesis of 4-fluoro-3-phenoxyphenylmethanol as an intermediate

To a stirred suspension of 1.4 grams (0.0375 mole) of lithium aluminum hydride in 50 mL of anhydrous diethyl ether was added dropwise during a one hour period a solution of 21.6 grams (0.1 mole) of 4-fluoro-3-phenoxybenzaldehyde in 50 mL of anhydrous diethyl ether. Upon completion of addition, the reaction mixture was heated at reflux for 1.0 hour. The reaction mixture was cooled to 15° C., and 1.4 mL of water was cautiously added dropwise. Upon completion of addition, the reaction mixture was again cooled to 15° C., and 1.4 mL of an aqueous, 15% sodium hydroxide solution was added dropwise, folowed by an additional 4.2 mL of water. The mixture was filtered through diatomaceous earth, and the filtrate was concentrated under reduced pressure, yielding 19.5 grams of 4-fluoro-3-phenoxyphenylmethanol as an oil.

Step G

Synthesis of 4-fluoro-3-phenoxyphenylmethyl chloride as an intermediate

To a stirred solution of 12.6 grams (0.106 mole) of thionyl chloride and a catalytic amount of pyridine in 25 mL of toluene was added dropwise during a 45 minute period a solution of 19.5 grams (0.88 mole) of 4-fluoro-3-phenoxyphenylmethanol (prepared in Step F) in 30 mL of toluene. The reaction mixture temperature was maintained at 25°-35° C. throughout the addition. Upon completion of addition, the reaction mixture was warmed to 45° C. where it stirred for one hour. The reaction mixture was cooled and then was concentrated under reduced pressure, yielding 23.5 grams of semi-solid. The semi-solid was combined with 114.2 grams of identical semi-solid obtained from a large run of the present reaction. The 136.6 grams of semi-solid was distilled under reduced pressure. The appropriate fractions were combined, yielding 100.3 grams of 4-fluoro-3-phenoxyphenylmethyl chloride, b.p. 98°–105° C./0.03–0.13 mm Hg.

Step H

Synthesis of (4-fluoro-3-phenoxyphenyl)methyltriphenylphosphonium chloride as an intermediate This compound was prepared in a manner analogous to that of Example 4, Step C, using 11.8 grams (0.05 mole) of 4-fluoro-3-phenoxyphenylmethyl chloride and 13.1 grams (0.05 mole) of triphenylphosphine in 100 mL of tetrahydrofuran. The yield of (4-fluoro-3-phenoxyphenyl)methyltriphenylphosphonium chloride was 15.0 grams.

Step I

Synthesis of 1-cyclopropyl-1-(4-trifluoromethylphenyl)-4-(4-fluoro-3-phenoxyphenyl)-1,3-butadiene (Compound A13) as an intermediate This compound was prepared in a manner analogous to that of Example 4, Step D, using 1.7 grams (0.0069 mole) of 3-cyclopropyl-3-(4-trifluoromethylphenyl)propenal (prepared in Step E of the present example), 3.4 grams (0.0069 mole) of (4-fluoro-3-phenoxyphenyl)methyltriphenylphosphonium chloride (prepared in Step H of the present example), and 2.8 mL (0.0069 mole) of n-butyllithium (2.5 molar in hexane) in 69 mL of dry tetrahydrofuran. The yield of 1-cyclopropyl-1-(4-trifluoromethylphenyl)-4-(4-fluoro-3-phenoxyphenyl)-1,3-butadiene was 1.8 grams. The nmr spectrum was consistent with the proposed structure.

Step J

Synthesis of 1-cyclopropyl-1-(4-trifluoromethylphenyl)-4-(4-fluoro-3-phenoxyphenyl)butane (Compound 99)

This compound was prepared in a manner analogous to that of Example 4, Step E, by the hydrogenation of 0.98 gram (0.0023 mole) of 1-cyclopropyl-1-(4-trifluoromethylphenyl)-4-(4-fluoro-3-phenoxyphenyl)-1,3-butadiene in the presence of 0.2 gram (0.00023 mole) of Raney nickel in 50 mL of ethanol. The yield of 1-cyclopropyl-1-(4-trifluoromethylphenyl)-4-(4-fluoro-3-phenoxyphenyl)butane was 0.65 gram as an oil. The nmr spectrum was consistent with the proposed structure.

EXAMPLE 6

Synthesis of
1-cyclopropyl-1-(4-ethoxyphenyl)-4-(3-phenoxyphenyl)butane [Compound 104]

Step A

Synthesis of cyclopropyl (4-ethoxyphenyl) ketone as an intermediate

Under an argon atmosphere a stirred suspension of 36.7 grams (0.275 mole) of aluminum chloride in 225 mL of carbon disulfide was cooled to 0° C., and 22.7 mL (0.25 mole) of cyclopropanecarboxylic acid chloride was added dropwise during a 15 minute period. During the addition and for 30 minutes after its completion the reaction mixture temperature was maintained at 0°–15° C. Then 34.8 mL of ethoxybenzene was added dropwise during a one hour period. The reaction mixture temperature was maintained at 5°–10° C. during this addition. Upon completion of addition, the reaction mixture was allowed to warm to ambient temperature as it stirred for one hour. Petroleum ether, 250 mL, was added to the reaction mixture, and the suspension was stirred for ten minutes. The solid was collected by filtration and washed with petroleum ether. The solid was returned to the reaction vessel and, with stirring, was cooled to 0°–10° C. while 50 mL of water was added dropwise during a 30 minute period. Upon completion of addition, the mixture was stirred until the evolution of hydrogen chloride ceased. An additional 250 mL of water was then added, and the mixture was stirred at ambient temperature for 30 minutes. It was then warmed to 80° C. where it stirred for an additional 30 minutes. The mixture was cooled, and a solid was collected by filtration. The solid was dissolved in methylene chloride, and the solution was dried with sodium sulfate. The mixture was filtered, and the filtrate was concentrated under reduced pressure to a residual solid. The solid was recrystallized from heptane, yielding, in two crops, 44.0 grams of cyclopropyl (4-ethoxyphenyl) ketone, m.p. 67°–70° C. The nmr spectrum was consistent with the proposed structure.

Step B

Synthesis of
1-cyclopropyl-1-(4-ethoxyphenyl)-2-propen-1-ol as an intermediate

This compound was prepared in a manner analogous to that of Example 4, Step A, using 5.7 grams (0.03 mole) of cyclopropyl (4-ethoxyphenyl) ketone and 33 mL (0.033 mole) of vinylmagnesium bromide (1.0M in tetrahydrofuran) in 30 mL of dry tetrahydrofuran. The yield of 1-cyclopropyl-1-(4-ethoxyphenyl)-2-propen-1-ol was 6.5 grams as an oil.

Step C

Synthesis of
3-cyclopropyl-3-(4-ethoxyphenyl)-propenal as an intermediate

This compound was prepared in a manner analogous to that of Example 4, Step B, using 6.5 grams (0.029 mole) of 1-cyclopropyl-1-(4-ethoxyphenyl)-2-propen-1-ol and 15.3 grams (0.029 mole) of pyridinium dichromate in 40 mL of methylene chloride. The yield of 3-cyclopropyl-3-(4-ethoxyphenyl)propenal was 4.2 grams as an oil.

Step D

Synthesis of
1-cyclopropyl-1-(4-ethoxyphenyl)-4-(3-phenoxyphenyl)-1,3-butadiene (Compound A15) as an intermediate This compound was prepared in a manner analogous to that of Example 4, Step D, using 4.2 grams (0.019 mole) of 3-cyclopropyl-3-(4-ethoxyphenyl)propenal, 9.1 grams (0.019 mole) of 3-phenoxyphenylmethyltriphenylphosphonium bromide (prepared as in Example 4, Step H), and 7.5 mL (0.019 mole) of n-butyllithium (2.5M in tetrahydrofuran) in 100 mL of dry tetrahydrofuran. The yield of 1-cyclopropyl-1-(4-ethoxyphenyl)-4-(3-phenoxyphenyl)-1,3-butadiene was 2.5 grams.

Step E

Synthesis of
1-cyclopropyl-1-(4-ethoxyphenyl)4-(3-phenoxyphenyl)butane (Compound 104)

This compound was prepared in a manner analogous to that of Example 4, Step E, by the hydrogenation of 1.5 grams (0.0039 mole) of 1-cyclopropyl-1-(4-ethoxyphenyl)-4-(3-phenoxyphenyl)-1,3-butadiene in the presence of 0.34 gram of Raney nickel in 70 mL of ethanol. The yield of 1-cyclopropyl-1-(4-ethoxyphenyl)-4-(3-phenoxyphenyl)butane was 1.2 grams as an oil. The nmr spectrum was consistent with the proposed structure.

EXAMPLE 7

Synthesis of
1-(4-chlorophenyl)-1-cyclopropyl4-(3-phenoxyphenyl)-butane [Compound 88]

Step A

Synthesis of ethyl 3-(3-phenoxyphenyl)acrylate

To a stirred solution of 23.4 g (0.188 mole) of 3-phenoxybenzaldehyde in 175 mL of 1,4-dioxane was added 45.2 grams (0.130 mole) of ethoxycarbonylmethylenetriphenylphosphorane in one portion. The reaction was allowed to stir at ambient temperature overnight. The solvent was evaporated under reduced pressure, leaving a residue which was dissolved in ethyl acetate. Approximately 30 grams of silica gel was mixed with this solution. This solvent was evaporated under reduced pressure, and the silica gel was placed in a sintered glass filter. The silica gel was eluted with 1000 mL of heptane/ethyl acetate (3:1). The solvent was evaporated under reduced pressure, leaving an oil. This oil was dissolved in 150 mL of heptane/ethyl acetate (9:1), treated with 15 grams of silica gel, and filtered. The filtrate was evaporated under reduced pressure, leaving 26.7 grams of ethyl 3-(3-phenoxyphenyl)acrylate as an oil. The nmr spectrum was consistent with the proposed structure.

Step B

Synthesis of 3-(3-phenoxyphenyl)propanol

To a stirred mixture of 7.4 grams (0.196 mole) of lithium aluminum hydride in 300 mL of dry diethyl ether under a nitrogen atmosphere was added 26.2 grams (0.098 mole) of ethyl 3-(3-phenoxyphenyl)acrylate in 300 mL of dry diethyl ether. The addition required 90 minutes to complete, and the reaction mixture was stirred overnight at ambient temperature. It was then cooled in an ice/water bath, and sequentially 14 mL of water, 14 mL of a 15% aqueous solution of sodium hydroxide, and 42 mL of water were all added dropwise. This mixture was filtered, and the filtrate was dried over anhydrous sodium sulfate. After being filtered, the solvent was evaporated under reduced pressure, leaving 21.9 grams of 3-(3-phenoxyphenyl)propanol as an oil. The nmr spectrum was consistent with the proposed structure.

Step C

Synthesis of 3-(3-phenoxyphenyl)propyl bromide

To a mixture of 21.0 grams (0.092 mole) of 3-(3-phenoxyphenyl)propanol and 1 mL of pyridine which had been cooled to 0° C. was added dropwise during a 20 minute period 8.27 grams (0.031 mole) of phosphorus tribromide. This mixture was stirred at 0° C. for 90 minutes and then at ambient temperature overnight. The reaction mixture was then diluted with 200 mL of diethyl ether, and the solution was washed successively twice with 50 mL of water, four times with 25 mL of a saturated, aqueous solution of sodium bicarbonate, once with 50 mL of water, and once with an aqueous solution of sodium chloride. After being dried over anhydrous sodium sulfate and filtered, the solvent was evaporated under reduced pressure, leaving 18.9 grams of 3-(3-phenoxyphenyl)propyl bromide as an oil. The nmr spectrum was consistent with the proposed structure.

Step D

Synthesis of 3-(3-phenoxyphenyl)propyltriphenylphosphonium bromide

Under nitrogen a mixture of 2.9 grams (0.01 mole) of 3-(3-phenoxyphenyl)propyl bromide and 2.9 grams (0.01 mole) of triphenylphosphine in 25 mL of acetonitrile was heated at reflux overnight. The solvent was evaporated under reduced pressure. Toluene was added to the residue, and this mixture was heated at reflux for 90 minutes during which a solid formed. Filtration yielded 4.2 grams of 3-(3-phenoxyphenyl)propyltriphenylphosphonium bromide, m.p. 198°–200° C.

Step E

Synthesis of 1-(4-chlorophenyl)-1-cyclopropyl-4-(3-phenoxyphenyl)-1-butene (Compound B7)

Under an argon atmosphere a slurry of 4.2 grams (0.0076 mole) of 3-phenoxyphenyl)propyltriphenylphosphonium bromide in 75 mL of freshly distilled tetrahydrofuran was cooled to 0° C. with stirring. To this mixture was added 5.4 mL (0.0079 mole ) of a 1.55M solution of n-butyllithium in hexanes in 0.5 mL portions using a syringe during a 20 minute period. An additional 2.0 mL (0.0031 mole) of the n-butyllithium solution was then added slowly, causing a red solution to form. This solution was allowed to warm to ambient temperature at which it was stirred for 60 minutes. This solution was again cooled to 0° C., and 1.3 grams (0.0072 mole) 4-chlorophenyl cyclopropyl ketone in 5 mL of tetrahydrofuran was added portionwise using a syringe. Upon completion of addition, the reaction mixture was allowed to warm to ambient temperature. A precipitate formed. After two hours the reaction mixture was filtered. To the filtrate was added 1 mL of water with stirring to decompose any residual n-butyllithium. The filtrate was dried over anhydrous sodium sulfate and was filtered. The filtrate was evaporated under reduced pressure, leaving a mixture of a solid and an oil as the residue. To this residue was addedheptane/ ethyl acetate (1:2) with stirring. A solid was removed by filtration, and the filtrate was concentrated under reduced pressure. Additional solid was removed by filtration from the concentrated solution. The filtrate was placed on a column of silica gel, eluting with 500 mL of heptane/ ethyl acetate (9:1). The appropriate fractions were combined, and the solvent was evaporated under reduced pressure, yielding 1.2 grams of 1-(4-chlorophenyl)-1-cyclopropyl-4-(3-phenoxyphenyl)-1-butene as an oil. The nmr spectrum was consistent with the proposed structure. Analysis for $C_{25}H_{23}ClO$ Calc'd: C 80.09; H 6.18; Found: C 80.15; H 5.98.

Step F

Synthesis of 1-(4-chlorophenyl)-1-cyclopropyl-4-(3-phenoxyphenyl)butane (Compound 88)

This compound was prepared in a manner analogous to that of Example 4, Step E, by hydrogenation of 1.0 gram (0.0027 mole) of 1-(4-chlorophenyl)-1-cyclopropyl-4-(3-phenoxyphenyl)-1-butene in the presence of 0.35 gram of Raney nickel in 75 mL of ethanol. This procedure yielded 0.8 gram of 1-(4-chlorophenyl)-1-cyclopropyl-4(3-phenoxyphenyl)butane as an a oil. The nmr spectrum was consistent with the proposed structure.

In the normal use of the insecticidal, pyrethroidlike compounds of the present invention, the compounds usually will not be employed free from admixture or dilution, but ordinarily will be used in a suitable formulated composition compatible with the method of application and comprising an insecticidally effective amount of pyrethroid-like compound. The compounds of this invention, like most pesticidal agents, may be blended with the agriculturally acceptable surfaceactive agents and carriers normally employed for facilitating the dispersion of active ingredients, recognizing the accepted fact that the formulation and mode of application of an insecticide may affect the activity of the material. The present pyrethroid-like compounds may be applied, for example, as sprays, dusts, or granules to the area where pest control is desired, the type of application varying of course with the pest and the environment. Thus, the compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the pyrethroid-like compounds. The granule particles are relatively large, a diameter of about 400-2500 microns typically. The particles are either impregnated with the compounds of this invention from solution or coated with these pyrethroid-like compounds, adhesive sometimes being employed. Granules generally contain 0.05-10%, preferably 0.5-5%, active ingredient as the insecticidally effective amount.

Dusts are admixtures of these pyrethroid-like compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of pyrethroid-like compound and 99 parts of talc.

The compounds of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5-50% pyrethroidlike compound, and 95-50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of (4-fluoro-3-phenoxyphenyl)methyl 2-cyclopropyl-2-(4trifluoromethoxyphenyl)ethyl ether and 72 parts of attapulgite clay.

Manufacturing concentrates are useful for shipping low melting compounds of this invention. Such concentrates are prepared by melting the low melting solid compounds together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrethroid-like compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfates of higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal composition.

Other useful formulations include simple solutions of the active ingredient in a solvent in which it is completely soluble at the desired concentrations, such as acetone or other organic solvents.

An insecticidally effective amount of pyrethroid-like compound in an insecticidal composition diluted for application is normally in the range of about 0.001% to about 8% by weight. Many variations of spraying and dusting compositions known in the art may be used by substituting the compounds of this invention into compositions known or apparent in the art.

The insecticidal and acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally and acaricidally effective amount of pyrethroid-like compound be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications an insecticidally effective amount will be about 75 to 4000 grams per hectare, preferably 150 grams to 3000 grams per hectare.

The insecticidal activity of the pyrethroid-like compound of this invention was evaluated as follows:

Foliar Evaluation

The compound was tested by foliar application at various concentrations in aqueous solutions containing 10% acetone and 0.25% octyl phenoxypolyethoxy ethanol. The evaluation utilized Mexican bean beetle (*Epilachna varivestis*), southern armyworm (*Spodootera eridania*), pea aphid (*Acyrthosiohon pisum*), cabbage looper (*Trichoplusia ni*), beet armyworm (*Spodootera exiqua*), and twospotted spider mite (*Tetranychus urticae*).

For all insects except pea aphid, pinto bean (*Phaseolus vuloaris*) plants were placed on a revolving turntable in a hood, and the test solutions were applied with a sprayer. The test solutions were applied to the upper and lower surfaces of the plant leaves to runoff. The plants were then allowed to dry and were severed at the base of the stem before being placed in cups. Ten individuals of the appropriate insect species were placed in each cup and the cup covered. Mortality was read 48 hours later.

Fava bean was substituted for pinto bean in the case of pea aphid, and the treated, potted plants were placed in cups infested with ten individuals and covered. Mortality was read 48 hours later.

Acaricidal tests were performed using the following procedure: Leaves infested with adult twospotted spider mites (*Tetranychus urticae*) were removed from culture plants and cut into segments containing 50-75 female mites. Each segment was placed on the upper leaf surface of a whole pinto bean plant. After the mites had migrated to the under surfaces of the leaves, the leaf segments used to infest were removed, and each plant was sprayed with test chemical as described above. After the plants had dried, the entire plant and pot were placed in metal trays in a hood, a supply of water in the tray keeping the plants turgid. After 48 hours the living and dead mites were counted, and percent mortality was calculated.

The results of these tests are shown in Table 4.

Soil Evaluation

A stock solution of the test compound was prepared by dissolving 9.6 mg in 10 mL of acetone and diluting with 90 mL of acetone/water (1:9). The addition of 5 mL of this stock solution to 30 grams of air-dried, clay loam soil in a three ounce plastic cup provided a concentration of 16 ppm of the test compound in the soil. Serial dilution of the stock solution was used to provide concentrations of the test compound in soil of 8, 4, 2, 1, 0.5, and 0.25 ppm. In all cases 5 mL of a solution having the required concentration was added to 30 grams of soil. The treated soil was allowed to stand uncovered in a hood for 0.5 hour to evaporate the acetone. Before infesting the soil with southern corn rootworm larvae (*Diabrotica undecimounctata howardi* Barber) the soil was mixed thoroughly, and two three-day-old corn sprouts were planted in it. Ten early third-stage (9-10 days old) southern corn rootworm larvae were placed in the cup which was covered with a plastic bag. After storage at 74°-78° F. for 48 hours, the mortality of the larvae was determined by removing the cup from the plastic bag, removing the cover, and placing the cup in a modified Berlese polyethylene funnel fitted with an 18-mesh screen. The funnels were placed over containers of an aqueous detergent solution. Incandescent lights (100 watts) were placed 36 cm above the soil samples. The heat from these lights slowly dried the soilcausing larvae that had not been affected by the test compound to emerge from the soil and drop into the detergent solution. The percent mortality was determined in this manner for each concentration.

Results of these tests are reported in Table 5.

Fish Toxicity

The toxicity towards fish was determined in a 48 hour static bioassay using the bluegill sunfish (*Lepomis macrochirus*). Three fish ranging in size from 1 to 2 inches were placed in a 0.95 liter jar containing the specified concentration of the compound. Two replicates were used for each concentration. After 48 hours the percent kill was determined. Concentrations of chemicals used were 6.3 ppm, 3.1 ppm, and occasionally 1.7 ppm. Compound 16, the compound of Example 1 and a preferred compound of this invention, exhibited 83% kill at 6.3 ppm. Another preferred compound, Compound 24, killed only 50% of the fish at the same concentration. By way of comparison, cypermethrin, a conventional pyrethroid insecticide used widely for crop protection, displays 100% kill at a concentration of 0.01 ppm.

The remarkably low toxicity towards fish of the pyrethroid-like compounds is certainly unexpected, and this factor, in combination with the demonstrated insecticidal activity, should make them appropriate compounds for control of insect infestations in aquatic environments, such as rice paddies.

TABLE 1

TABLE OF ETHERS, THIOETHERS, AND BUTANE DERIVATIVES

Ar—CH—CH$_2$—Z—CH$_2$—Ar'

| Cmpd No. | Ar | Z | Ar' |
|---|---|---|---|
| 1 | phenyl | O | 2-methyl[1,1'-biphenyl]-3-yl |
| 2 | phenyl | O | 3-phenoxyphenyl |
| 3 | phenyl | O | 4-fluoro-3-phenoxyphenyl |
| 4 | 4-fluorophenyl | O | 2-methyl[1,1'-biphenyl]-3-yl |
| 5 | 4-fluorophenyl | O | 3-phenoxyphenyl |
| 6 | 4-fluorophenyl | O | 4-fluoro-3-phenoxyphenyl |
| 7 | 2-chlorophenyl | O | 2-methyl[1,1'-biphenyl]-3-yl |
| 8 | 2-chlorophenyl | O | 3-phenoxyphenyl |
| 9 | 2-chlorophenyl | O | 4-fluoro-3-phenoxyphenyl |
| 10 | 3-chlorophenyl | O | 2-methyl[1,1'-biphenyl]-3-yl |
| 11 | 3-chlorophenyl | O | 3-phenoxyphenyl |
| 12 | 3-chlorophenyl | O | 4-fluoro-3-phenoxyphenyl |
| 13 | 4-chlorophenyl | O | 2-methyl[1,1'-biphenyl]-3-yl |
| 14 | 4-chlorophenyl | O | 3-phenoxyphenyl |
| 15 | 4-chlorophenyl | O | 3-phenoxyphenyl (Stereoisomer B)[a] |
| 16 | 4-chlorophenyl | O | 4-fluoro-3-phenoxyphenyl |

TABLE 1-continued
TABLE OF ETHERS, THIOETHERS, AND BUTANE DERIVATIVES

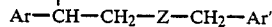

Ar—CH—CH₂—Z—CH₂—Ar'

| Cmpd No. | Ar | Z | Ar' |
|---|---|---|---|
| 17 | 4-chlorophenyl | O | 4-fluoro-3-phenoxyphenyl (Stereoisomer A)[b] |
| 18 | 4-chlorophenyl | O | 4-fluoro-3-phenoxyphenyl (Stereoisomer B)[c] |
| 19 | 4-chlorophenyl | S | 2-methyl[1,1'-biphenyl]-3-yl |
| 20 | 4-chlorophenyl | S | 3-phenoxyphenyl |
| 21 | 4-chlorophenyl | S | 4-fluoro-3-phenoxyphenyl |
| 22 | 4-bromophenyl | O | 2-methyl[1,1'-biphenyl]-3-yl |
| 23 | 4-bromophenyl | O | 3-phenoxyphenyl |
| 24 | 4-bromophenyl | O | 4-fluoro-3-phenoxyphenyl |
| 25 | 4-methylphenyl | O | 2-methyl[1,1'-biphenyl]-3-yl |
| 26 | 4-methylphenyl | O | 3-phenoxyphenyl |
| 27 | 4-methylphenyl | O | 4-fluoro-3-phenoxyphenyl |
| 28 | 3-ethylphenyl | O | 2-methyl[1,1'-biphenyl]-3-yl |
| 29 | 3-ethylphenyl | O | 3-phenoxyphenyl |
| 30 | 3-ethylphenyl | O | 4-fluoro-3-phenoxyphenyl |
| 31 | 4-ethylphenyl | O | 2-methyl[1,1'-biphenyl]-3-yl |
| 32 | 4-ethylphenyl | O | 3-phenoxyphenyl |
| 33 | 4-ethylphenyl | O | 4-fluoro-3-phenoxyphenyl |
| 34 | 4-t-butylphenyl | O | 2-methyl[1,1'-biphenyl]-3-yl |
| 35 | 4-t-butylphenyl | O | 3-phenoxyphenyl |
| 36 | 4-t-butylphenyl | O | 4-fluoro-3-phenoxyphenyl |
| 37 | 4-trifluoromethylphenyl | O | 2-methyl[1,1'-biphenyl]-3-yl |
| 38 | 4-trifluoromethylphenyl | O | 3-phenoxyphenyl |
| 39 | 4-trifluoromethylphenyl | O | 4-fluoro-3-phenoxyphenyl |
| 40 | 4-methoxyphenyl | O | 2-methyl[1,1'-biphenyl]-3-yl |
| 41 | 4-methoxyphenyl | O | 3-phenoxyphenyl |
| 42 | 4-methoxyphenyl | O | 4-fluoro-3-phenoxyphenyl |
| 43 | 4-ethoxyphenyl | O | 2-methyl[1,1'-biphenyl]-3-yl |
| 44 | 4-ethoxyphenyl | O | 3-phenoxyphenyl |
| 45 | 4-ethoxyphenyl | O | 4-fluoro-3-phenoxyphenyl |
| 46 | 4-difluoromethoxyphenyl | O | 2-methyl[1,1'-biphenyl]-3-yl |
| 47 | 4-difluoromethoxyphenyl | O | 3-phenoxyphenyl |
| 48 | 4-difluoromethoxyphenyl | O | 4-fluoro-3-phenoxyphenyl |
| 49 | 4-trifluoromethoxyphenyl | O | 2-methyl[1,1'-biphenyl]-3-yl |
| 50 | 4-trifluoromethoxyphenyl | O | 3-phenoxyphenyl |
| 51 | 4-trifluoromethoxyphenyl | O | 4-fluoro-3-phenoxyphenyl |
| 52 | 4-(2-fluoroethoxy)phenyl | O | 2-methyl[1,1'-biphenyl]-3-yl |
| 53 | 4-(2-fluoroethoxy)phenyl | O | 3-phenoxyphenyl |
| 54 | 4-(2-fluoroethoxy)phenyl | O | 4-fluoro-3-phenoxyphenyl |
| 55 | 4-trifluoromethylthiophenyl | O | 2-methyl[1,1'-biphenyl]-3-yl |
| 56 | 4-trifluoromethylthiophenyl | O | 3-phenoxyphenyl |
| 57 | 4-trifluoromethylthiophenyl | O | 4-fluoro-3-phenoxyphenyl |
| 58 | 4-trifluoromethylsulfinylphenyl | O | 2-methyl[1,1'-biphenyl]-3-yl |
| 59 | 4-trifluoromethylsulfinylphenyl | O | 3-phenoxyphenyl |
| 60 | 4-trifluoromethylsulfinylphenyl | O | 4-fluoro-3-phenoxyphenyl |
| 61 | 4-trifluoromethylsulfonylphenyl | O | 2-methyl[1,1'-biphenyl]-3-yl |
| 62 | 4-trifluoromethylsulfonylphenyl | O | 3-phenoxyphenyl |
| 63 | 4-trifluoromethylsulfonylphenyl | O | 4-fluoro-3-phenoxyphenyl |
| 64 | 1,3-benzodioxol-5-yl | O | 2-methyl[1,1'-biphenyl]-3-yl |
| 65 | 1,3-benzodioxol-5-yl | O | 3-phenoxyphenyl |
| 66 | 1,3-benzodioxol-5-yl | O | 4-fluoro-3-phenoxyphenyl |
| 67 | 2,2-difluoro-1,3-benzo-dioxol-5-yl | O | 2-methyl[1,1'-biphenyl]-3-yl |
| 68 | 2,2-difluoro-1,3-benzo-dioxol-5-yl | O | 3-phenoxyphenyl |
| 69 | 2,2-difluoro-1,3-benzo-dioxol-5-yl | O | 4-fluoro-3-phenoxyphenyl |
| 70 | 3-chloro-4-methoxyphenyl | O | 2-methyl[1,1'-biphenyl]-3-yl |
| 71 | 2,3-dihydro-2,2-dimethyl-benzofuran-5-yl | O | 2-methyl[1,1'-biphenyl]-3-yl |
| 72 | 2,3-dihydro-2,2-dimethyl-benzofuran-5-yl | O | 3-phenoxyphenyl |
| 73 | 2,3-dihydro-2,2-dimethyl-benzofuran-5-yl | O | 4-fluoro-3-phenoxyphenyl |
| 74 | 2,2,3,3-tetrafluoro-benzofuran-5-yl | O | 2-methyl[1,1'-biphenyl]-3-yl |
| 75 | 2,2,3,3-tetrafluoro-benzofuran-5-yl | O | 3-phenoxyphenyl |
| 76 | 2,2,3,3-tetrafluoro-benzofuran-5-yl | O | 4-fluoro-3-phenoxyphenyl |
| 77 | 2-thienyl | O | 2-methyl[1,1'-biphenyl]-3-yl |
| 78 | 2-thienyl | O | 3-phenoxyphenyl |

TABLE 1-continued

TABLE OF ETHERS, THIOETHERS, AND BUTANE DERIVATIVES

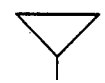
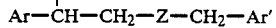

| Cmpd No. | Ar | Z | Ar' |
|---|---|---|---|
| 79 | 2-thienyl | O | 4-fluoro-3-phenoxyphenyl |
| 80 | 4-chlorophenyl | O | 6-phenoxy-2-pyridyl |
| 81 | 4-ethoxyphenyl | O | 6-phenoxy-2-pyridyl |
| 82 | 2-chlorophenyl | $CH_2$ | 3-phenoxyphenyl |
| 83 | 2-chlorophenyl | $CH_2$ | 4-fluoro-3-phenoxyphenyl |
| 84 | 3-chlorophenyl | $CH_2$ | 2-methyl[1,1'-biphenyl]-3-yl |
| 85 | 3-chlorophenyl | $CH_2$ | 3-phenoxyphenyl |
| 86 | 3-chlorophenyl | $CH_2$ | 4-fluoro-3-phenoxyphenyl |
| 87 | 4-chlorophenyl | $CH_2$ | 2-methyl[1,1'-biphenyl]-3-yl |
| 88 | 4-chlorophenyl | $CH_2$ | 3-phenoxyphenyl |
| 89 | 4-chlorophenyl | $CH_2$ | 4-fluoro-3-phenoxyphenyl |
| 90 | 4-chlorophenyl | $CH_2$ | 6-phenoxy-2-pyridyl |
| 91 | 4-bromophenyl | $CH_2$ | 2-methyl[1,1'-biphenyl]-3-yl |
| 92 | 4-bromophenyl | $CH_2$ | 3-phenoxyphenyl |
| 93 | 4-bromophenyl | $CH_2$ | 4-fluoro-3-phenoxyphenyl |
| 94 | 4-methylphenyl | $CH_2$ | 2-methyl[1,1'-biphenyl]-3-yl |
| 95 | 4-methylphenyl | $CH_2$ | 3-phenoxyphenyl |
| 96 | 4-methylphenyl | $CH_2$ | 4-fluoro-3-phenoxyphenyl |
| 97 | 4-trifluoromethylphenyl | $CH_2$ | 2-methyl[1,1'-biphenyl]-3-yl |
| 98 | 4-trifluoromethylphenyl | $CH_2$ | 3-phenoxyphenyl |
| 99 | 4-trifluoromethylphenyl | $CH_2$ | 4-fluoro-3-phenoxyphenyl |
| 100 | 4-methoxyphenyl | $CH_2$ | 2-methyl[1,1'-biphenyl]-3-yl |
| 101 | 4-methoxyphenyl | $CH_2$ | 3-phenoxyphenyl |
| 102 | 4-methoxyphenyl | $CH_2$ | 4-fluoro-3-phenoxyphenyl |
| 103 | 4-ethoxyphenyl | $CH_2$ | 2-methyl[1,1'-biphenyl]-3-yl |
| 104 | 4-ethoxyphenyl | $CH_2$ | 3-phenoxyphenyl |
| 105 | 4-ethoxyphenyl | $CH_2$ | 4-fluoro-3-phenoxyphenyl |
| 106 | 4-difluoromethoxyphenyl | $CH_2$ | 2-methyl[1,1'-biphenyl]-3-yl |
| 107 | 4-difluoromethoxyphenyl | $CH_2$ | 3-phenoxyphenyl |
| 108 | 4-difluoromethoxyphenyl | $CH_2$ | 4-fluoro-3-phenoxyphenyl |
| 109 | 4-trifluoromethoxyphenyl | $CH_2$ | 2-methyl[1,1'-biphenyl]-3-yl |
| 110 | 4-trifluoromethoxyphenyl | $CH_2$ | 3-phenoxyphenyl |
| 111 | 4-trifluoromethoxyphenyl | $CH_2$ | 4-fluoro-3-phenoxyphenyl |
| 112 | 4-(2-fluoroethoxy)phenyl | $CH_2$ | 2-methyl[1,1'-biphenyl]-3-yl |
| 113 | 4-(2-fluoroethoxy)phenyl | $CH_2$ | 3-phenoxyphenyl |
| 114 | 4-(2-fluoroethoxy)phenyl | $CH_2$ | 4-fluoro-3-phenoxyphenyl |
| 115 | 1,3-benzodioxol-5-yl | $CH_2$ | 2-methyl[1,1'-biphenyl]-3-yl |
| 116 | 1,3-benzodioxol-5-yl | $CH_2$ | 3-phenoxyphenyl |
| 117 | 1,3-benzodioxol-5-yl | $CH_2$ | 4-fluoro-3-phenoxyphenyl |
| 118 | 2,2-difluoro-1,3-benzo-dioxol-5-yl | $CH_2$ | 2-methyl[1,1'-biphenyl]-3-yl |
| 119 | 2,2-difluoro-1,3-benzo-dioxol-5-yl | $CH_2$ | 3-phenoxyphenyl |
| 120 | 2,2-difluoro-1,3-benzo-dioxol-5-yl | $CH_2$ | 4-fluoro-3-phenoxyphenyl |
| 121 | 4-trifluoromethylthiophenyl | $CH_2$ | 2-methyl[1,1'-biphenyl]-3-yl |
| 122 | 4-trifluoromethylthiophenyl | $CH_2$ | 3-phenoxyphenyl |
| 123 | 4-trifluoromethylthiophenyl | $CH_2$ | 4-fluoro-3-phenoxyphenyl |
| 124 | 2,3-dihydro-2,2-dimethyl-benzofuran-5-yl | $CH_2$ | 2-methyl[1,1'-biphenyl]-3-yl |
| 125 | 2,3-dihydro-2,2-dimethyl-benzofuran-5-yl | $CH_2$ | 3-phenoxyphenyl |
| 126 | 2,3-dihydro-2,2-dimethyl benzofuran-5-yl | $CH_2$ | 4-fluoro-3-phenoxyphenyl |
| 127 | 2,2,3,3-tetrafluoro-benzofuran-5-yl | $CH_2$ | 2-methyl[1,1'-biphenyl]-3-yl |
| 128 | 2,2,3,3-tetrafluoro-benzofuran-5-yl | $CH_2$ | 3-phenoxyphenyl |
| 129 | 2,2,3,3-tetrafluoro-benzofuran-5-yl | $CH_2$ | 4-fluoro-3-phenoxyphenyl |
| 130 | 2-thienyl | $CH_2$ | 3-phenoxyphenyl |
| 131 | 2-thienyl | $CH_2$ | 4-fluoro-3-phenoxyphenyl |
| 132 | 4-ethoxyphenyl | $CH_2$ | 6-phenoxy-2-pyridyl |

[a] $[\alpha]_D^{25} = (-)26.20°$ in $CHCl_3$
[b] $[\alpha]_D^{25} = (+)22.19°$ in $CHCl_3$
[c] $[\alpha]_D^{25} = (-)20.64°$ in $CHCl_3$

TABLE 2
INSECTICIDAL AND ACARICIDAL 1,4-DIARYL-1-CYCLOPROPYL-1,3-BUTADIENE DERIVATIVES

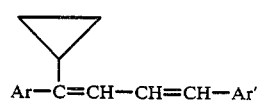

Ar—C=CH—CH=CH—Ar'

| Cmpd No. | Ar | Ar' |
|---|---|---|
| A1 | 3-chlorophenyl | 2-methyl[1,1'-biphenyl]-3-yl |
| A2 | 3-chlorophenyl | 3-phenoxyphenyl |
| A3 | 3-chlorophenyl | 4-fluoro-3-phenoxyphenyl |
| A4 | 4-chlorophenyl | 2-methyl[1,1'-biphenyl]-3-yl |
| A5 | 4-chlorophenyl | 3-phenoxyphenyl |
| A6 | 4-chlorophenyl | 4-fluoro-3-phenoxyphenyl |
| A7 | 4-chlorophenyl | 6-phenoxy-2-pyridyl |
| A8 | 4-methylphenyl | 2-methyl[1,1'-biphenyl]-3-yl |
| A9 | 4-methylphenyl | 3-phenoxyphenyl |
| A10 | 4-methylphenyl | 4-fluoro-3-phenoxyphenyl |
| A11 | 4-trifluoromethylphenyl | 2-methyl[1,1'-biphenyl]-3-yl |
| A12 | 4-trifluoromethylphenyl | 3-phenoxyphenyl |
| A13 | 4-trifluoromethylphenyl | 4-fluoro-3-phenoxyphenyl |
| A14 | 4-ethoxyphenyl | 2-methyl[1,1'-biphenyl]-3-yl |
| A15 | 4-ethoxyphenyl | 3-phenoxyphenyl |
| A16 | 4-ethoxyphenyl | 4-fluoro-3-phenoxyphenyl |
| A17 | 4-trifluoromethoxyphenyl | 2-methyl[1,1'-biphenyl]-3-yl |
| A18 | 4-trifluoromethoxyphenyl | 3-phenoxyphenyl |
| A19 | 4-trifluoromethoxyphenyl | 4-fluoro-3-phenoxyphenyl |
| A20 | 1,3-benzodioxol-5-yl | 2-methyl[1,1'-biphenyl]-3-yl |
| A21 | 1,3-benzodioxol-5-yl | 3-phenoxyphenyl |
| A22 | 1,3-benzodioxol-5-yl | 4-fluoro-3-phenoxyphenyl |
| A23 | 2,3-dihydro-2,2-dimethyl-benzofuran-5-yl | 2-methyl[1,1'-biphenyl]-3-yl |
| A24 | 2,3-dihydro-2,2-dimethyl-benzofuran-5-yl | 3-phenoxyphenyl |
| A25 | 2,3-dihydro-2,2-dimethyl-benzofuran-5-yl | 4-fluoro-3-phenoxyphenyl |
| A26 | 2-thienyl | 2-methyl[1,1-biphenyl]-3-yl |
| A27 | 2-thienyl | 3-phenoxyphenyl |
| A28 | 2-thienyl | 4-fluoro-3-phenoxyphenyl |

TABLE 3
INSECTICIDAL AND ACARICIDAL 1,4-DIARYL-CYCLOPROPYL-1-BUTENE DERIVATIVES

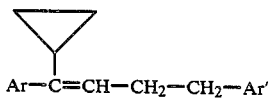

Ar—C=CH—CH$_2$—CH$_2$—Ar'

| Cmpd No. | Ar | Ar' |
|---|---|---|
| B1 | phenyl | 4-fluoro-3-phenoxyphenyl |
| B2 | 4-fluorophenyl | 3-phenoxyphenyl |
| B3 | 4-fluorophenyl | 4-fluoro-3-phenoxyphenyl |
| B4 | 2-chlorophenyl | 2-methyl[1,1'-biphenyl]-3-yl |
| B5 | 2-chlorophenyl | 3-phenoxyphenyl |
| B6 | 2-chlorophenyl | 4-fluoro-3-phenoxyphenyl |
| B7 | 4-chlorophenyl | 3-phenoxyphenyl |
| B8 | 4-chlorophenyl | 4-fluoro-3-phenoxyphenyl |
| B9 | 4-bromophenyl | 3-phenoxyphenyl |
| B10 | 4-ethylphenyl | 2-methyl[1,1'-biphenyl]-3-yl |
| B11 | 4-ethylphenyl | 4-fluoro-3-phenoxyphenyl |
| *B12 | 4-methoxyphenyl | 3-phenoxyphenyl |
| **B13 | 4-methoxyphenyl | 3-phenoxyphenyl |
| B14 | 4-difluoromethoxyphenyl | 2-methyl[1,1'-biphenyl]-3-yl |
| B15 | 4-difluoromethoxyphenyl | 3-phenoxyphenyl |
| B16 | 4-difluoromethoxyphenyl | 4-fluoro-3-phenoxyphenyl |
| B17 | 4-(2-fluoroethoxy)phenyl | 3-phenoxyphenyl |
| B18 | 4-(2-fluoroethoxy)phenyl | 4-fluoro-3-phenoxyphenyl |
| B19 | 4-trifluoromethylthio-phenyl | 2-methyl[1,1'-biphenyl]-3-yl |
| B20 | 4-trifluoromethylthio-phenyl | 3-phenoxyphenyl |
| B21 | 4-trifluoromethylthio-phenyl | 4-fluoro-3-phenoxyphenyl |

TABLE 3-continued
INSECTICIDAL AND ACARICIDAL 1,4-DIARYL-CYCLOPROPYL-1-BUTENE DERIVATIVES

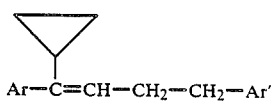

Ar—C=CH—CH$_2$—CH$_2$—Ar'

| Cmpd No. | Ar | Ar' |
|---|---|---|
| B22 | 2,2-difluoro-1,3-benzo-dioxol-5-yl | 2-methyl[1,1'-biphenyl]-3-yl |
| B23 | 2,2-difluoro-1,3-benzo-dioxol-5-yl | 3-phenoxyphenyl |
| B24 | 2,2-difluoro-1,3-benzo-dioxol-5-yl | 4-fluoro-3-phenoxyphenyl |
| B25 | 2,2,3,3-tetrafluorobenzo-furan-5-yl | 2-methyl[1,1'-biphenyl]-3-yl |
| B26 | 2,2,3,3-tetrafluorobenzo-furan-5-yl | 3-phenoxyphenyl |
| B27 | 2,2,3,3-tetrafluorobenzo-furan-5-yl | 4-fluoro-3-phenoxyphenyl |

*Mixture of 57% Z isomer and 43% E isomer by gas chromatographic analysis (area %)
**Mixture of 86% Z isomer and 14% E isomer by gas chromatographic analysis (area %)

TABLE 4
FOLIAR INSECTICIDAL TEST RESULTS

| Cmpd No. | Rate (ppm) | % Kill BAW | MBB | SAW | TSM | CL | PA |
|---|---|---|---|---|---|---|---|
| 1 | 500 | | | | 9 | | 0 |
| | 100 | 45 | 0 | | | 20 | |
| 2 | 500 | | | 23 | | | 5 |
| | 100 | 95 | 95 | | | 55 | |
| 3 | 500 | | | | 20 | | 25 |
| | 100 | 100 | 100 | | | 85 | |
| 4 | 1000 | | | | | | 15 |
| | 250 | | 85 | | | 85 | |
| 5 | 500 | | | | | | 70 |
| | 250 | | 100 | | | 95 | |
| 6 | 1000 | | | | | | 60 |
| | 250 | | 100 | | | 100 | |
| 10 | 1000 | | 35 | | 29 | 95 | 50 |
| 11 | 1000 | | 100 | | 55 | 100 | 100 |
| 12 | 1000 | | 100 | | 100 | 100 | 90 |
| 13 | 1000 | | 100 | 100 | 100 | | 100 |
| | 100 | 90 | | | | 50 | |
| 14 | 1000 | | 100 | 100 | 90[a] | | 100 |
| | 100 | 100 | | | | 95 | |
| 15 | 1000 | | 100 | | | 100 | 90 |
| 16 | 1000 | | 100 | 100 | 100 | | 100 |
| | 100 | 100 | | | | 100 | |
| 17 | 500 | | | | 38 | | 100 |
| | 100 | | 75 | 95 | | | |
| | 50 | 90 | | | | 95 | |
| 18 | 500 | | | | 83 | | 100 |
| | 100 | | 100 | 100 | | | |
| | 50 | 100 | | | | 100 | |
| 19 | 1000 | | | | 11 | | |
| | 500 | | 45 | | | | |
| | 250 | | | | | 100 | 20 |
| 20 | 500 | | | | 12 | | |
| | 250 | | 95 | | | 100 | 75 |
| 21 | 500 | | | | 15 | | |
| | 250 | | 100 | | | 100 | 90 |
| 22 | 1000 | 100 | 80 | | 60 | | 70 |
| | 500 | | | | | 95 | |
| 23 | 1000 | 100 | 100 | | 77 | | 100 |
| | 500 | | | | | 100 | |
| 24 | 1000 | 100 | | | 100 | | 80 |
| | 500 | | | | | 100 | |
| 25 | 1000 | | 100 | | 0 | | 35 |
| | 500 | 100 | | | | 100 | |
| 26 | 1000 | | 100 | | 0 | | 45 |
| | 500 | 100 | | | | 100 | |
| 27 | 1000 | | 100 | | 40 | | 35 |
| | 500 | 100 | | | | 100 | |

TABLE 4-continued
FOLIAR INSECTICIDAL TEST RESULTS

| Cmpd No. | Rate (ppm) | BAW | MBB | SAW | TSM | CL | PA |
|---|---|---|---|---|---|---|---|
| 34 | 500 | | | | | | 25 |
| | 100 | 35 | 70 | | 16 | 10 | |
| 35 | 500 | | | | 99[a] | | 90 |
| | 100 | 55 | 100 | | | 0 | |
| 36 | 500 | | | | 100 | | 60 |
| | 100 | 55 | 100 | | | 45 | |
| 37 | 1000 | | 100 | | 100 | 100 | 100 |
| 38 | 1000 | | 100 | | 100 | 100 | 100 |
| 39 | 1000 | | 100 | | 100 | 95 | 90 |
| 40 | 1000 | 100 | 100 | | 40 | | 80 |
| | 500 | | | | | 75 | |
| 41 | 1000 | | 100 | 100 | 0 | | 100 |
| | 500 | 95 | | | | 85 | |
| 42 | 1000 | | 75 | 100 | 0 | | 100 |
| | 500 | 100 | | | | 100 | |
| 43 | 500 | 100 | 100 | | 0 | 100 | 0 |
| 44 | 500 | 100 | 100 | | 0 | 100 | 60 |
| 45 | 1000 | | | | 100 | | |
| | 500 | 100 | 100 | | | 100 | 90 |
| 46 | 1000 | | 80 | 100 | 95 | 90 | |
| 47 | 1000 | | 70 | 100 | 100 | 100 | |
| 48 | 1000 | | 95 | 100 | 100 | 100 | |
| 49 | 1000 | | 100 | 100 | 100 | 100 | |
| 50 | 1000 | | 100 | 100 | 100 | 100 | |
| 51 | 1000 | | 100 | 100 | 100 | 100 | |
| 52 | 1000 | | | | | | 0 |
| | 250 | | 75 | | 85 | | |
| 53 | 1000 | | | | | 55 | |
| | 250 | | 100 | | 100 | | |
| 54 | 1000 | | | | | 65 | |
| | 250 | | 90 | | 100 | | |
| 64 | 500 | | | 23 | | | |
| | 250 | | 85 | | 100 | 80 | |
| 65 | 500 | | | 1 | | | |
| | 250 | | 90 | | 100 | 70 | |
| 66 | 250 | | 100 | 11 | 100 | 65 | |
| 70 | 500 | 100 | 80 | 1 | 40 | 0 | |
| 77 | 500 | | | 14 | | 0 | |
| | 100 | 0 | 0 | | 0 | | |
| 78 | 500 | | | 11 | | 0 | |
| | 100 | 20 | 0 | | 0 | | |
| 79 | 500 | | | 10 | | 0 | |
| | 100 | 45 | 15 | | 0 | | |
| 80 | 1000 | | 95 | 96 | 100 | 100 | |
| 84 | 1000 | | 95 | 21 | 90 | 65 | |
| 85 | 1000 | | 100 | 14 | 100 | 95 | |
| 86 | 1000 | | 80 | 92 | 100 | 85 | |
| 87 | 1000 | | 100 | 97 | 100 | 90 | |
| 88 | 1000 | | 100 | 100 | 100 | 80 | |
| 89 | 1000 | | 100 | 100 | 100 | 100 | |
| 94 | 1000 | | 100 | 63 | 100 | 35 | |
| 95 | 1000 | | 100 | 50 | 100 | 55 | |
| 96 | 1000 | | 100 | 100 | 100 | 40 | |
| 97 | 1000 | | 100 | 99 | 100 | 100 | |
| 98 | 1000 | | 100 | 100 | 100 | 100 | |
| 99 | 1000 | | 100 | 100 | 100 | 100 | |
| 103 | 1000 | | 95 | 100 | 85 | 95 | |
| 104 | 1000 | | 100 | 89 | 100 | 60 | |
| 105 | 1000 | | 100 | 100 | 100 | 95 | |
| 109 | 1000 | | 100 | 100 | 100 | 80 | |
| 110 | 1000 | | 100 | 100 | 100 | 100 | |
| 111 | 1000 | | 100 | 100 | 100 | 100 | |
| A4 | 1000 | | 63[a] | | 0 | 5 | 0 |
| A6 | 1000 | | 68[a] | | 0 | 25 | 0 |
| A8 | 1000 | | 0 | | 0 | 0 | 0 |
| A9 | 1000 | | 0 | | 0 | 0 | 0 |
| A10 | 1000 | | 0 | | 0 | 30 | 0 |
| A11 | 1000 | | 68[a] | | 0 | 88[a] | 0 |
| A12 | 1000 | | 78[a] | | 0 | 68[a] | 0 |
| A13 | 1000 | | 95[a] | | 0 | 100[a] | 0 |
| A15 | 1000 | | 55 | | 0 | 60 | 0 |
| B7 | 1000 | | 90 | | 0 | | 0 |
| | 500 | 95 | | | | 30 | |
| B8 | 1000 | | | | 0 | | 100 |
| | 500 | 95 | 100 | | | 100 | |
| B9 | 1000 | | 65 | | 0 | | 0 |
| | 500 | 100 | | | | 35 | |
| B12 | 500 | 100 | 100 | | 0 | 20 | 30 |
| B13 | 1000 | | 65 | | 0 | 0 | 0 |

[a] Average of two tests
BAW = beet armyworm
MBB = Mexican bean beetle
SAW = southern armyworm
TSM = twospotted spider mite
CL = cabbage looper
PA = pea aphid

TABLE 5
SOIL INSECTICIDAL TEST RESULTS

| Cmpd. No. | Rate (ppm) | Initial % Kill SCR |
|---|---|---|
| 13 | 16 | 15 |
| 14 | 2 | 25 |
| 16 | 16 | 50 |
| 22 | 16 | 35 |
| 26 | 16 | 90 |
| 27 | 16 | 70 |
| 40 | 16 | 45 |
| 41 | 16 | 65 |
| 42 | 16 | 75[a] |
| 48 | 15 | 100 |
| 80 | 15 | 85 |
| 85 | 15 | A[b] |
| 88 | 15 | A |
| 89 | 15 | 80 |
| 94 | 15 | A |
| 95 | 15 | A |
| 96 | 15 | A |
| 99 | 15 | A |
| 103 | 15 | 85 |
| 105 | 15 | A |
| 110 | 15 | A |
| B7 | 15 | 60 |
| B8 | 15 | 60 |
| B9 | 15 | 30 |

[a] Average of two tests.
[b] A = active = >75% kill
SCR = southern corn rootworm

We claim:

1. A compound of the formula

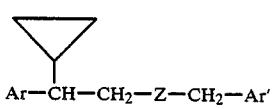

in which Ar is a phenyl or thieynl group which may be substituted by $(C_{1-6})$alkyl, halo, $(C_{1-4})$haloalkyl, $(C_{1-4})$alkoxy, $(C_{1-4})$haloalkoxy, or by a substituent having the structure $-A-(CR^1R^2)-A-$ where $R^1$ and $R^2$ are independently hydrogen, halogen, or $(C_{1-2})$alkyl, n is 1 or 2, and each A is O or $CH_2$ and is bonded to an adjacent carbon atom of the aromatic ring; Z is oxygen, sulfur, or methylene; and Ar' is phenoxylphenyl, 2-methyl[1,1'-biphenyl]-3-yl, or 6-phenoxy-2-pyridyl each optionally substituted with halo or lower alkyl.

2. A compound of claim 1 in which Ar' is 3-phenoxyphenyl, 4-fluoro-3-phenoxyphenyl, 2-methyl[1,1'-biphenyl]-3-yl, or 6-phenoxy-2-pyridyl.

3. A compound of claim 2 in which Ar is selected from phenyl, $(C_{1-6})$alkylphenyl, halophenyl, $(C_{1-4})$haloalkylphenyl, $(C_{1-4})$alkoxyphenyl, $(C_{1-4})$haloalkoxyphenyl, and 1,3-benzodioxol-5-yl.

4. A compound of claim 3 in which Ar' is 3-phenoxyphenyl; Z is oxygen; and Ar is selected from phenyl, 4-fluorophenyl, 3-chlorophenyl, 4-chlorophenyl, 4-bromophenyl, 4-methylphenyl, 4-t-butylphenyl, 4-trifluoromethylphenyl, 4-methoxyphenyl, 4-ethoxyphenyl, 4-(2-fluoroethoxy)phenyl, 4-difluoromethoxyphenyl, 4-trifluoromethoxyphenyl and 1,3-benzodioxol-5-yl.

5. A compound of claim 4 in which Ar is 4-chlorophenyl for which $[\alpha]_D^{25}$ in chloroform is negative.

6. A compound of claim 4 in which Ar is 4-trifluoromethylphenyl.

7. A compound of claim 4 in which Ar is 4-trifluoromethylphenyl.

8. A compound of claim 3 in which Ar' is 4-fluoro-3-phenoxyphenyl; Z is oxygen; and Ar is selected from 4-fluorophenyl, 3-chlorophenyl, 4-chlorophenyl, 4-bromophenyl, 4-methylphenyl, 4-t-butylphenyl, 4-trifluoromethylphenyl, 4-methoxyphenyl, 4-ethoxylphenyl, 4-(2-fluoroethoxy)phenyl, 4-difluoromethoxyphenyl, 4-trifluoromethoxyphenyl, and 1,3-benzodioxol-5-yl.

9. A compound of claim 8 in which Ar is 4-chlorophenyl.

10. A compound of claim 9 for which $[\alpha]_D^{25}$ in chloroform is negative.

11. A compound of claim 8 in which Ar is 4-trifluoromethylphenyl.

12. A compound of claim 8 in which Ar is 4-ethoxyphenyl.

13. A compound of claim 8 in which Ar is 4-trifluoromethoxyphenyl.

14. A compound of claim 3 in which Ar, is 2-methyl[1,1,'-biphenyl]-3-yl; Z is oxygen; and Ar is selected from phenyl, 4-fluorophenyl, 3chlorophenyl, 4-chlorophenyl, 4-bromophenyl, 4-methylphenyl, 4-t-butylphenyl, 4-trifluoromethylphenyl, 4-methoxyphenyl, 4-ethoxyphenyl, 4-(2-fluoroethoxy)phenyl, 4-difluoromethoxyphenyl, 4-trifluoromethoxyphenyl, and 1,3-benzodioxol-5-yl.

15. A compound of claim 14 in which Ar is 4-trifluoromethoxyphenyl.

16. A compund of claim 3 in which Ar is 4-chlorophenyl; Z is sulfur; and Ar' is selected from 3-phenoxyphenyl, 4-fluoro-3-phenoxyphenyl, and 2-methyl[1,1'-biphenyl]-3-yl.

17. A compound of claim 16 in which Ar' is 4-fluoro-3-phenoxyphenyl.

18. A compound of claim 3 in which Ar' is 6-phenoxy-2-pyridyl, Z is oxygen, and Ar is 4-chlorophenyl.

19. A compound of claim 3 in which Ar' is selected from 3-phenoxyphenyl, 4-fluoro-3-phenoxyphenyl, and 2-methyl[1,1'-biphenyl]-3-yl; Z is methylene; and Ar is selected from 3-chlorophenyl, 4-chlorophenyl,4-methylphenyl, 4-ethoxyphenyl, and 4trifluoromethoxyphenyl.

20. A compound of claim 19 in which Ar' is 3-phenoxyphenyl and Ar is 4-chlorophenyl.

21. A compound of claim 19 in which Ar' is 3-phenoxyphenyl and Ar is 4-trifluoromethylphenyl.

22. A compound of claim 19 in which Ar' is 4-fluoro-3-phenoxyphenyl and Ar is 4-chlorophenyl.

23. A compound of claim 19 in which Ar' is 4-fluoro-3-phenoxyphenyl and Ar is 4-trifluoromethylphenyl.

24. A compound of claim 19 in which Ar' is 4-fluoro-3-phenoxyphenyl and Ar is 4-trifluoromethoxyphenyl.

25. A compound of claim 19 in which Ar' is 2-methyl[1,1'-biphenyl]-3-yl and Ar is 4-trifluoromethylphenyl.

26. A compound of the formula

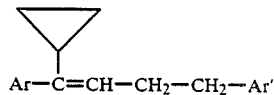

in which Ar is a pheny or thienyl group which may be substituted by $(C_{1-6})$alkyl, halo, $(C_{1-4})$haloalkyl, $(C_{1-4})$alkoxy, $(C_{1-4})$haloalkoxy, or by a substituent having the structure $—A—(CR^1R^2)—A—$ where $R^1$ and $R^2$ are independently hydrogen, halogen, or $(C_{1-2})$alkyl, n is 1 or 2, and each A is O or $CH_2$ and is bonded to an adjacent carbon atom of the aromatic ring; and Ar' is a phenoxyphenyl, 2-methyl[1,1,'-biphenyl]-3-yl, or 6-phenoxy-2-pyridyl each optionally substituted with halo or lower alkyl.

27. A compound of claim 26 in which Ar' is selected from 3-phenoxyphenyl and 4-fluoro-3-phenoxyphenyl and Ar is selected from 4-chlorophenyl, 4-bromophenyl, and 4-methoxyphenyl.

28. A compound of claim 27 in which Ar' is 4-fluoro-3-phenoxyphenyl and Ar is 4-chlorophenyl.

29. A compound of the formula

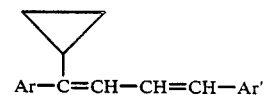

in which Ar is a phenyl or thienyl group which may be substituted by $(C_{1-6})$alkyl, halo, $(C_{1-4})$haloalkyl, $(C_{1-4})$alkoxy, $(C_{1-4})$haloalkoxy, or by a substituent having the structure $—A—(CR^1R^2)—A—$ where $R^1$ and $R^2$ are independently hydrogen, halogen, or $(C_{1-2})$alkyl, n is 1 or 2, and each A is O or $CH_2$ and is bonded to an adjacent carbon atom of the aromatic ring; and Ar' is phenoxyphenyl, 2-methyl[1,1'-biphenyl]-3-yl, or 6-phenoxy-2-pyridyl each optionally substituted with halo or lower alkyl.

30. A compound of claim 29 in which Ar' is selected from 3-phenoxyphenyl, 4-fluoro-3-phenoxyphenyl, and 2-methyl[1,1'-biphenyl]-3 -yl and Ar is selected from 4-chlorophenyl, 4-methylphenyl, 4-trifluoromethylphenyl, and 4-ethoxyphenyl.

31. An insecticidal or acaricidal composition comprising an insecticidally or acaricidally effective amount of a compound of claim 2 in admixture with one or more compatible agriculatural carriers, diluents, adjuvants, or complementary pesticides.

32. An insecticidal composition comprising an insecticidally effective amount of a compound of claim 26 in admixture with one or more compatible agricultural carriers, diluents, adjuvants, or complementary pesticides.

33. An insecticidal composition comprising an insecticidally effective amount of a compound of claim 27 in admixture with one or more compatible agriculatural carriers, diluents, adjuvants, or complementary pesticides.

34. A method of controlling insects and acarids by applying to the locus where control is desired an insecticidally or acaricidally effective amount of a compound of claim 1.

35. A method of controlling insects by applying to the locus where control is desired an insecticidally effective amount of a compound of claim 26.

36. A method of controlling insects by applying to the locus where control is desired an insecticidally effective amount of a compound of claim 29.

* * * * *

UNITED STATES PATENT AND TRADEMARK OFFICE
CERTIFICATE OF CORRECTION

PATENT NO. : 4,808,762

DATED : February 28, 1989

INVENTOR(S) : Gary A. Meier, Scott M. Sieburth, Thomas G. Cullen, and John F. Engel It is certified that error appears in the above-identified patent and that said Letters Patent is hereby corrected as shown below:

Column 34, claim 1, line 53, "-A-$(CR^1R^2)$-A-" should read ---A-$(CR^1R^2)_n$-A---.
Column 35, claim 14, line 41, "3chlorophenyl," should read --3-chlorophenyl,--, and claim 19, line 65, "4trifluoromethox-" should read --4-trifluoromethox---. Column 36, claim 26, line 24, "-A-$(CR^1R^2)$-A-" should read ---A-$(CR^1R^2)_n$-A---, claim 29, line 50, "-A-$(CR^1R^2)$-A-" should read ---A-$(CR^1R^2)_n$-A---, claim 30, line 60, "2-methyl[1,1'biphenyl]-3 -yl" should read --2-methyl[1,1'biphenyl]-3-yl--.

Signed and Sealed this

Twenty-ninth Day of May, 1990

Attest:

HARRY F. MANBECK, JR.

Attesting Officer

Commissioner of Patents and Trademarks